(12) United States Patent
Graetz et al.

(10) Patent No.: US 9,783,568 B2
(45) Date of Patent: *Oct. 10, 2017

(54) SALTS OF HIV INHIBITOR COMPOUNDS

(71) Applicant: Gilead Sciences, Inc., Foster City, CA (US)

(72) Inventors: Benjamin R. Graetz, San Mateo, CA (US); Richard Polniaszek, Menlo Park, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/170,728

(22) Filed: Jun. 1, 2016

(65) Prior Publication Data

US 2016/0355543 A1 Dec. 8, 2016

Related U.S. Application Data

(63) Continuation of application No. 14/585,011, filed on Dec. 29, 2014, now Pat. No. 9,381,206, which is a continuation of application No. 14/150,677, filed on Jan. 8, 2014, now Pat. No. 8,951,986, which is a continuation of application No. 12/999,441, filed as application No. PCT/US2009/049838 on Jul. 7, 2009, now Pat. No. 8,658,617.

(60) Provisional application No. 61/078,989, filed on Jul. 8, 2008.

(51) Int. Cl.
*A61K 31/7076* (2006.01)
*A61K 45/06* (2006.01)
*C07H 19/20* (2006.01)
*A61K 9/20* (2006.01)

(52) U.S. Cl.
CPC ............ *C07H 19/20* (2013.01); *A61K 9/20* (2013.01); *A61K 31/7076* (2013.01); *A61K 45/06* (2013.01)

(58) Field of Classification Search
None
See application file for complete search history.

(56) References Cited

U.S. PATENT DOCUMENTS

| | | |
|---|---|---|
| 4,649,041 A | 3/1987 | Peters et al. |
| 4,665,074 A | 5/1987 | Amschler |
| 4,816,570 A | 3/1989 | Farquhar |
| 4,968,788 A | 11/1990 | Farquhar |
| 5,260,440 A | 11/1993 | Hirai et al. |
| 5,378,474 A | 1/1995 | Morella et al. |
| 5,413,996 A | 5/1995 | Bodor |
| 5,455,339 A | 10/1995 | Chu |
| 5,466,793 A | 11/1995 | Honda et al. |
| 5,493,030 A | 2/1996 | Morgans, Jr. et al. |
| 5,585,397 A | 12/1996 | Tung et al. |
| 5,633,279 A | 5/1997 | Morgans, Jr. et al. |
| 5,654,286 A | 8/1997 | Hostetler |
| 5,656,745 A | 8/1997 | Bischofberger et al. |
| 5,663,159 A | 9/1997 | Starrett, Jr. et al. |
| 5,670,497 A | 9/1997 | Bold et al. |
| 5,744,600 A | 4/1998 | Mansuri et al. |
| 5,747,498 A | 5/1998 | Schnur et al. |
| 5,750,343 A | 5/1998 | Maag et al. |
| 5,750,493 A | 5/1998 | Sommadossi et al. |
| 5,792,756 A | 8/1998 | Starrett, Jr. et al. |
| 5,795,909 A | 8/1998 | Shashoua et al. |
| 5,804,559 A | 9/1998 | Budt et al. |
| 5,811,422 A | 9/1998 | Lam et al. |
| 5,874,577 A | 2/1999 | Chen et al. |
| 5,914,332 A | 6/1999 | Sham et al. |
| 5,962,684 A | 10/1999 | Vince et al. |
| 6,018,049 A | 1/2000 | Hajima et al. |
| 6,072,053 A | 6/2000 | Vince et al. |
| 6,174,888 B1 | 1/2001 | McQuire et al. |
| 6,290,994 B1 | 9/2001 | Lazaro Flores et al. |
| 6,312,662 B1 | 11/2001 | Erion et al. |
| 6,319,946 B1 | 11/2001 | Hale et al. |
| 6,395,763 B1 | 5/2002 | Stamos et al. |
| 6,555,676 B2 | 4/2003 | Gosselin et al. |
| 6,581,606 B2 | 6/2003 | Kutzko et al. |
| 6,602,902 B2 | 8/2003 | Shashoua et al. |
| 6,608,027 B1 | 8/2003 | Tsantrizos et al. |
| 6,761,903 B2 | 7/2004 | Chen et al. |
| 6,767,900 B2 | 7/2004 | Ubasawa et al. |
| 6,844,349 B2 | 1/2005 | Kath et al. |
| 6,858,618 B2 | 2/2005 | Raza et al. |
| 6,872,827 B2 | 3/2005 | Webb et al. |
| 6,962,684 B2 | 11/2005 | Kawazu et al. |

(Continued)

FOREIGN PATENT DOCUMENTS

| | | |
|---|---|---|
| AU | 779816 B2 | 2/2005 |
| CN | 101031306 A | 9/2007 |

(Continued)

OTHER PUBLICATIONS

Abdel-Meguid, S.S. et al. (1993). "Inhibition of Human Immunodeficiency Virus-1 Protease by a C2-Symmetric Phosphinate. Synthesis and CrystallographicAnalysis," Biochemistry 32(31):1543-1572.
African Regional Office Action mailed on Mar. 14, 2014, for African Regional Patent Application No. AP/P/2010/005509, filed Jul. 7, 2009, 5 pages.
African Search Report mailed on Sep. 27, 2011, for African Patent No. AP-2629, issued on Mar. 28, 2013, 1 page.
Alexander, J. et al. (Jan. 19, 1996). "Investigation of (Oxodioxolenyl)Methyl Carbamates as Nonchiral Bioreversible Prodrug Moieties for Chiral Amines," J. Med. Chem. 39(2):480-486.
Allen, L.F. et al. (Oct. 2003). "CI-1040 (PDI84352), a Targeted Signal Transduction Inhibitor of MEK (MAPKK)," in Seminars in Oncology, Elsevier Inc., 30(5):105-116.

(Continued)

*Primary Examiner* — Traviss C McIntosh, III
(74) *Attorney, Agent, or Firm* — Gilead Sciences, Inc.

(57) ABSTRACT

The invention is related to salts of anti-viral compounds, compositions containing such salts, and therapeutic methods that include the administration of such salts, as well as to process and intermediates useful for preparing such salts.

10 Claims, 6 Drawing Sheets

(56) References Cited

U.S. PATENT DOCUMENTS

| | | |
|---|---|---|
| 7,084,123 B2 | 8/2006 | Fujikura et al. |
| 7,169,766 B2 | 1/2007 | Sommadossi et al. |
| 7,273,715 B2 | 9/2007 | McDermott |
| 7,273,716 B2 | 9/2007 | McDermott |
| 7,273,717 B2 | 9/2007 | McDermott |
| 7,300,924 B2 | 11/2007 | Boojamra et al. |
| 7,319,148 B2 | 1/2008 | Marliere et al. |
| 7,358,261 B2 | 4/2008 | Carson et al. |
| 7,407,965 B2 | 8/2008 | Chen et al. |
| 7,417,055 B2 | 8/2008 | Cannizzaro et al. |
| 7,427,624 B2 | 9/2008 | Chen et al. |
| 7,427,636 B2 | 9/2008 | Cannizzaro et al. |
| 7,429,564 B2 | 9/2008 | Arbit et al. |
| 7,429,565 B2 | 9/2008 | Boojamra et al. |
| 7,432,261 B2 | 10/2008 | Cannizzaro et al. |
| 7,432,273 B2 | 10/2008 | Fardis et al. |
| 7,452,901 B2 | 11/2008 | Boojamra et al. |
| 7,462,608 B2 | 12/2008 | Chen et al. |
| 7,470,724 B2 | 12/2008 | Cannizzaro et al. |
| 7,645,747 B2 | 1/2010 | Boojamra et al. |
| 7,649,015 B2 | 1/2010 | Arimili et al. |
| 7,871,991 B2 | 1/2011 | Boojamra et al. |
| 7,871,992 B2 | 1/2011 | Jomaa et al. |
| 7,971,991 B2 * | 7/2011 | Davidson .......... B29C 67/0077 118/308 |
| 8,022,083 B2 | 9/2011 | Boojamra et al. |
| 8,318,701 B2 | 11/2012 | Boojamra et al. |
| 8,329,926 B2 | 12/2012 | Boojamra et al. |
| 8,658,617 B2 * | 2/2014 | Graetz ............ C07H 19/20 514/47 |
| 8,951,986 B2 * | 2/2015 | Graetz ............ C07H 19/20 514/47 |
| 9,381,206 B2 * | 7/2016 | Graetz ............ C07H 19/20 |
| 2001/0031773 A1 | 10/2001 | Camden |
| 2002/0051805 A1 | 5/2002 | Ueki et al. |
| 2002/0103378 A1 | 8/2002 | Ellis |
| 2002/0119443 A1 | 8/2002 | Becker et al. |
| 2002/0156133 A1 | 10/2002 | Bartholomaeus et al. |
| 2003/0045583 A1 | 3/2003 | Hadfield et al. |
| 2003/0109498 A1 | 6/2003 | Yuasa et al. |
| 2003/0149044 A1 | 8/2003 | Quallich et al. |
| 2004/0121316 A1 | 6/2004 | Birkus et al. |
| 2004/0157793 A1 | 8/2004 | Stuyver et al. |
| 2004/0167096 A1 | 8/2004 | Cheng et al. |
| 2005/0037925 A1 | 2/2005 | Tsukamoto et al. |
| 2005/0171126 A1 | 8/2005 | Torii et al. |
| 2005/0202054 A1 | 9/2005 | Faryniarz et al. |
| 2006/0069060 A1 | 3/2006 | Redkar et al. |
| 2006/0079478 A1 | 4/2006 | Boojamra et al. |
| 2006/0094870 A1 | 5/2006 | Torii et al. |
| 2006/0223794 A1 | 10/2006 | Bourghol Hickey et al. |
| 2006/0223820 A1 | 10/2006 | Brand et al. |
| 2006/0281759 A1 | 12/2006 | de Diego et al. |
| 2007/0049754 A1 | 3/2007 | Boojamra et al. |
| 2007/0149479 A1 | 6/2007 | Fischer et al. |
| 2007/0149552 A1 | 6/2007 | Ku et al. |
| 2007/0191482 A1 | 8/2007 | Choi et al. |
| 2007/0225249 A1 | 9/2007 | Shi |
| 2008/0207620 A1 | 8/2008 | Desai et al. |
| 2008/0221213 A1 | 9/2008 | Christgau |
| 2008/0226731 A1 | 9/2008 | Vasanthavada et al. |
| 2008/0279932 A1 | 11/2008 | Reber et al. |
| 2009/0012037 A1 | 1/2009 | Boojamra et al. |
| 2009/0163449 A1 | 6/2009 | Wempe |
| 2009/0202470 A1 | 8/2009 | Boojamra et al. |
| 2009/0275535 A1 | 11/2009 | Boojamra et al. |
| 2010/0093667 A1 | 4/2010 | Graetz et al. |
| 2011/0288053 A1 | 11/2011 | Boojamra et al. |
| 2013/0090299 A1 | 4/2013 | Boojamra et al. |
| 2013/0090302 A1 | 4/2013 | Boojamra et al. |
| 2013/0316969 A1 | 11/2013 | Boojamra et al. |

FOREIGN PATENT DOCUMENTS

| | | |
|---|---|---|
| DE | 4138584 | 5/1993 |
| EA | 014685 | 12/2010 |
| EP | 0 267 050 A2 | 5/1988 |
| EP | 0347852 | 12/1989 |
| EP | 0 369 409 A1 | 5/1990 |
| EP | 0 441 192 A2 | 8/1991 |
| EP | 0 465 297 A1 | 1/1992 |
| EP | 0 468 119 A1 | 1/1992 |
| EP | 0 468 866 A1 | 1/1992 |
| EP | 0 531 597 A1 | 3/1993 |
| EP | 0 632 048 A1 | 1/1995 |
| EP | 0 786 455 A1 | 7/1997 |
| EP | 0 852 233 A1 | 7/1998 |
| EP | 0 919 562 A1 | 6/1999 |
| EP | 1 295 879 A1 | 3/2003 |
| EP | 1778249 A2 | 5/2007 |
| EP | 1832582 A1 | 9/2007 |
| EP | 2305680 A2 | 4/2011 |
| JP | 2-178295 | 7/1990 |
| JP | H-03-5439 A | 1/1991 |
| JP | 4330086 B1 | 11/1992 |
| JP | 2007-502329 A | 2/2007 |
| RU | 2106353 | 3/1998 |
| RU | 2188203 | 8/2002 |
| WO | WO-8806158 A1 | 8/1988 |
| WO | WO-9119721 A1 | 12/1991 |
| WO | WO-9200988 | 1/1992 |
| WO | WO-9203452 A1 | 3/1992 |
| WO | WO-9213869 | 8/1992 |
| WO | WO-9218520 A1 | 10/1992 |
| WO | WO-9312123 A1 | 6/1993 |
| WO | WO-9324510 A1 | 12/1993 |
| WO | WO-9421604 A1 | 9/1994 |
| WO | WO-9507920 A1 | 3/1995 |
| WO | WO-9614314 A2 | 5/1996 |
| WO | WO-9615111 A1 | 5/1996 |
| WO | WO-9640156 A1 | 12/1996 |
| WO | WO-9701558 A1 | 1/1997 |
| WO | WO-9804569 A1 | 2/1998 |
| WO | WO-9811906 A1 | 3/1998 |
| WO | WO-9815563 A1 | 4/1998 |
| WO | WO-9929702 | 6/1999 |
| WO | WO-9933815 A1 | 7/1999 |
| WO | WO-9962921 A1 | 12/1999 |
| WO | WO-0004033 A1 | 1/2000 |
| WO | WO-0052015 A2 | 9/2000 |
| WO | WO-0056734 A1 | 9/2000 |
| WO | WO-0113957 A2 | 3/2001 |
| WO | WO-0117982 A1 | 3/2001 |
| WO | WO-0119320 A2 | 3/2001 |
| WO | WO-0139724 A2 | 6/2001 |
| WO | WO-0146204 A1 | 6/2001 |
| WO | WO-0164693 A1 | 9/2001 |
| WO | WO-0196329 A1 | 12/2001 |
| WO | WO-0196354 A1 | 12/2001 |
| WO | WO-0203997 | 1/2002 |
| WO | WO-0206292 | 1/2002 |
| WO | WO-0208241 | 1/2002 |
| WO | WO-0214344 A2 | 2/2002 |
| WO | WO-0248165 A2 | 6/2002 |
| WO | WO-02057425 | 7/2002 |
| WO | WO-02100415 A2 | 12/2002 |
| WO | WO-02103008 A2 | 12/2002 |
| WO | WO-03028737 A1 | 4/2003 |
| WO | WO-03050129 A1 | 6/2003 |
| WO | WO-03059255 A2 | 7/2003 |
| WO | WO-03064383 A2 | 8/2003 |
| WO | WO-03066005 A2 | 8/2003 |
| WO | WO-03080078 A1 | 10/2003 |
| WO | WO-03090690 | 11/2003 |
| WO | WO-03090691 A2 | 11/2003 |
| WO | WO-030091264 | 11/2003 |
| WO | WO-2004096233 A2 | 11/2004 |
| WO | WO-2004096234 A2 | 11/2004 |
| WO | WO-2004096235 A2 | 11/2004 |
| WO | WO-2004096236 A2 | 11/2004 |
| WO | WO-2004096237 A2 | 11/2004 |

(56) References Cited

FOREIGN PATENT DOCUMENTS

| WO | WO-2004096285 A2 | 11/2004 |
|---|---|---|
| WO | WO-2004096286 A2 | 11/2004 |
| WO | WO-2004096287 A2 | 11/2004 |
| WO | WO-2004096818 A2 | 11/2004 |
| WO | WO-2004100960 A2 | 11/2004 |
| WO | WO-2005000786 A1 | 1/2005 |
| WO | WO-2005002626 A2 | 1/2005 |
| WO | WO-2005011709 A1 | 2/2005 |
| WO | WO-2005012324 A2 | 2/2005 |
| WO | WO-2005039552 A2 | 5/2005 |
| WO | WO-2005042772 A1 | 5/2005 |
| WO | WO-2005042773 A1 | 5/2005 |
| WO | WO-2005044279 A1 | 5/2005 |
| WO | WO-2005044308 A1 | 5/2005 |
| WO | WO-2005047898 A2 | 5/2005 |
| WO | WO-2005063258 A1 | 7/2005 |
| WO | WO-2005063751 A1 | 7/2005 |
| WO | WO-2005064008 A1 | 7/2005 |
| WO | WO-2006015261 A2 | 2/2006 |
| WO | WO-2006015262 A2 | 2/2006 |
| WO | WO-2006051261 A1 | 5/2006 |
| WO | WO-2006110157 A2 | 10/2006 |
| WO | WO-2010005986 A1 | 1/2010 |
| WO | WO-2014055603 A1 | 4/2014 |
| WO | WO-2014055618 A1 | 4/2014 |

OTHER PUBLICATIONS

Anan'Eva, L.G. et al. (1983). "(2-Iodoethl) Phosphonic Derivatives," J. Gen. Chem. USSR 53(3):480-483.

Anderson, R.C. et al. (1984). "2-Chloro-4(R), 5(R)-Dimethyl-2-Oxo-1,3,2-Dioxaphospholane, a New Chiral Derivatizing Agent," J. Org. Chem. 49:1304-1305.

Anonymous. (Oct. 31, 2006). CAS Registry No. 182550-46-5, Search Date: Apr. 20, 2011.

Anonymous. (Oct. 31, 2006). CAS Registry No. 182550-51-2, Search Date: Apr. 20, 2011.

Asante-Appiah, E. et al. (1999). "HIV-1 Integrase: Structural Organization, Conformational Changes, and Catalysis," *Advances in Virus Research* 52:351-363.

Avert. (2010). "HIV and AIDS Vaccine," located at <http://www.avert.org/aids-vaccine.htm>, last visited on Sep. 16, 2013, 8 pages.

Balsiger, R.W. et al. (1959). "Synthesis of Potential Anticancer Agents. XVIII. Analogs of Carbamoyl Phosphate," J. Org. Chem. 24:434-436.

Balthazor, T.M. et al. (1980). "Nickel-Catalyzed Arbuzov Reaction: Mechanistic Observations," *J. Org. Chem.* 45:5425-5426.

Bantia, S. et al. (2001). "Purine Nucleoside Phosphorylase Inhibitor BCX-1777 (Immucillin-H)—A Novel Potent and Orally Active Immunosuppressive Agent," in International Immunopharmacology, Elsevier Science B.V., pp. 1199-1210.

Barre-Sinoussi, F. (1996). "HIV as the Cause of AIDS," *Lancet* 348:31-35.

Beauchamp, L.M. et al. (1996). "Guanine, Pyrazolo[3,4-d]pyrimidine, and Triazolo[4,5-d]pyrimidine(8-Azaguanine) Phosphonate Acyclic Derivatives as Inhibitors of Purine Nucleoside Phosphorylase," in Journal of Medicinal Chemistry, American ChemicalSociety, pp. 949-956.

Benzaria, S. et al. (1996). "Synthesis, in Vitro Antiviral Evaluation, and Stability Studies of Bis(S-acyl-2-thioethyl) Ester Derivatives of 9-[2.-(Phosphonomethoxy)ethyl]adenine (PMEA) as Potential PMEA Prodrugs with Improved Oral Bioavailabitity," J. Med. Chem. 39:4958-4965.

Berge, S.M. et al. (1977). "Pharmaceutical Salts," *J. of Pharm. Sciences* 66(1):1-19.

Beusen, D.D. et al. (1995). "Solid-State Nuclear Magnetic Resonance Analysis of the Conformation of an Inhibitor Bound to Thermolysin," *J. Med. Chem.* 38(14):2742-2747.

Birkus et al. (2007). "Cathepsin A is the Major Hydrolase Catalyzing the Intracellular Hydrolysis of the Antiretroviral Nucleotide Phosphonoamidate Prodrugs GS-7340 and GS-9131," Antimicrob. Agents Chemother. 51(2):543-550.

Borhani, D.W. et al. (2004). "A-420983: A Potent, Orally Active Inhibitor of Ick With Efficacy in a Model of Transplant Rejection," Bioorganic & Medicinal Chemistry Letters 14:2613-2616.

Bowker, M.J. (2002). "A Procedure for Salt Selection and Optimization," Chapter 7 in Handbook of Pharmaceutical Salts: Properties, Selection, and Use, pp. 161-189.

Bundgaard, H. (1985). *Design of Prodrugs,* Elsevier Science Ltd, pp. 70-74.

Bundgaard, H. et al. (1991). "Design and Application of Prodrugs," in Drug Design and Development, pp. 113-191.

Burger, A. et al. (1957). "Monoesters and Ester-Amidates of Aromatic Phosphonic Acids," *J. Am. Chem. Society* 79:3575-3579.

Bzowska, A. et al. (2000). Purine Nucleoside Phosphorylases: Properties, Functions, and Clinical Aspects, in Pharmacology & Therapeutics, vol. 88, Elsevier Science, Inc., pp. 349-425.

Campagne, J. et al. (1993). "Synthesis of Mixed Phosphonate Diester Analogues of Dipeptides Using BOP or PyBOP Reagents," *Tetrahedron Letters* 34(42):6743-6744.

Campagne, J. et al. (1995). "(1H-Benzotriazol-1-yloxy)tris(dimethylamino)phosphonium Hexafluorophosphate- and (1H-Benzotriazol-1-yloxy)tripyrrolidinophosphonium Hexafluorophosphate-Mediated Activation," J. Org. Chem. 60(16):5214-5223.

Campbell, D. (1992). "The Synthesis of Phosphonate Esters, an Extension of the Mitsunobu Reaction," *J. Org. Chem.* 57:6331-6335.

Carter, H.E. et al. (1965). "Carbobenzoxy Chloride and Derivatives," Org. Synth. Coll. 3:167-169.

Casara, P.J. et al. (1992). "Synthesis of Acid Stable 5'-0-Fluoromethyl Phosphonates of Nucleosides, Evaluation as Inhibitors of Reverse Transcriptase," *Bioorg. Med. Chem. Letters* 2(2):145-148.

Casteel, D.A. et al. (Sep. 1991). "Steric and Electronic Effects in the Aryl Phosphate to Arylphosphonate Rearrangement," Synthesis 691-693.

Cavalier, J. et al. (Jan. 1998). "New Highly Diastereoselective Synthesis of Phosphoramidates. A Route to Chiral Methyl p-Nitrophenyl Alkyphosphonates," Synlett 1:73-75.

CDC: Centers for Disease Control and Prevention: Pre-Exposure Prophylaxis (PrEP). (2013), located at <http://www.cdc.gov/hiv/prep/>, last visited on Sep. 15, 2013, 4 pages.

Chapman, H. et al. (2001). "Practical Synthesis, Separation, and Stereochemical Assignment of the PMPA Pro-Drug GS-7340," in *Nucleosides, Nucleotides & Nucleic Acids,* vol. 20, Nos. 4-7, Marcel Dekker, Inc., pp. 621-628.

Chen, S. et al. (1997). "Design, Synthesis, and Biochemical Evaluation of Phosphonate and Phosphonamidate Analogs of Glutathionylspermidine as Inhibitors of Glutathionylspermidine Synthetase/Amidase from *EscherIchia coli*," J. Med. Chem. 40(23):3842-3850.

Chilean Office Action mailed on Jul. 14, 2014, for Chilean Patent Application No. 14-2011 filed on Jul. 7, 2009, 5 pages.

Chinese Office Action mailed on Mar. 17, 2013 for Chinese Patent Application No. 200980126248.X filed on Jul. 7, 2009, 7 pages.

Chong, Y. et al. (2002). "Stereoselective Synthesis and Antiviral Activity of D-2',3'-Didehydro-2',3'-Dideoxy-2'-Fluoro-4'-Thionucleosides," J. Med. Chem. 45:4888-4898.

Chong, Y. et al. (2004). "Effects of Fluorine Substitution of Cytosine Analogues on the Binding Affinity to HIV-1 Reverse Transcriptase," *Bioorganic & Medicinal Chemistry Letters* 14(2):437-440.

Chong, Y. et al. (May-Aug. 2003). "2'-Fluoro-4'-thio-2',3'-unsaturated nucleosides: anti-HIV activity, resistance profile, and molecular modeling studies," Nucleosides, Nucleotides & Nucleic Acids 22(5-8):611-615.

Choo, H. et al. (Jan. 30, 2003). "Synthesis, Anti-HIV Activity, and Molecular Mechanism of Drug Resistance of L-2',3'-Didehydro-2',3'-Dideoxy-2'-Fluoro-4'-Thionucleosides," J. Med. Chem. 46(3):389-398.

Clark, J.L. et al. "Mycophenolic Acid Analogues as Potential Agents Against West Nile Virus Infection."

(56) References Cited

OTHER PUBLICATIONS

Coe, D.M. et al. (1991). "Synthesis of Some Mimics of Nucleoside Triphosphates," J. Chem. Soc., Chem. Commun. 312-314.
Coleman, R. et al. (1992). "Synthesis of the Aziridino [1,2-a] Pyrrolidine Substructure of the Antitumor Agents Azinomycin A and B," J. Org. Chem. 57(22):5813-5815.
Columbian Office Action mailed on Dec. 6, 2013, for Columbian Patent Application No. 10.159887, filed on Jul. 7, 2009, 8 pages.
Columbian Office Action mailed on Feb. 6, 2013, for Columbian Patent Application No. 10.159887, filed on Jul. 7, 2009, 13 pages. (with English Translation).
Conklyn, M. et al. (Dec. 2004, e-pub. Sep. 15, 2004). "The JAK3 Inhibitor CP-690550 Selectively Reduces NK and CD5+ Cell Numbers in Cynomolgus Monkey Blood Following Chronic Oral Dosing," Journal of Leukocyte Biology 76(6):1248-1255.
Laflamme et al. (2007). "Novel 2'-Fluoro Substituted Nucleotide HIV Reverse Transcriptase Inhibitor GS-9148 Exhibits Low Potential for Mitochondrial Toxicity In Vitro". 47th Interscience Conference on Antimicrobial Agents and Chemotherapy, Chicago.
D'Addona, D. et al. (2001). "Preparation of Carbamates from Amines and Alcohols Under Mild Conditions," Tetrahedron Letters 42:5227-5229.
Davies, L.C. et al. (1988). "Dinucleotide Analogues as Inhibitors of Thymidine Kinase, Thymidylate Kinase, and Ribonucleotide Reductase," J. Med. Chem. 31:1305-1308.
De Clercq, E. (1994). "New Developments in the Chemotherapy of Lentivirus (Human Immunodeficiency Virus) Infections: Sensitivity/Resistance of HIV-1 to Non-Nucleoside HIV-1-Specific Inhibitors," Annals of the NY Academy of Sciences 724:438-456.
De Clercq, E. (2001). "New Developments in Anti-HIV Chemotherapy," Current Medicinal Chemistry 8(13):1543-1572.
De Clercq, E. (2002). "Highlights in the Development of New Antiviral Agents," in Mini Reviews in Medicinal Chemistry, Bentham Science Publishers, Ltd. 2(2):163-175.
De Lombaert, S. et al. (1994). "N-Phosphonomethyl Dipeptides and Their Phosphonate Prodrugs, a New Generation of Neutral Endopeptidase (NEP, EC 3.4.24.11) Inhibitors," J. Med. Chem. 37:498-511.
Dvorakova, H. (Aug. 16, 1996). "Synthesis of 2'-Aminomethyl Derivatives of N-(2-(Phosphonomethoxy)ethyl) Nucleotide Analogues as Potential Antiviral Agents," J. Med. Chem. 39(17):3263-3268.
Effenberger, F. et al. (1985). "2(1 H)-Pyridon als Austrittsgruppe bei Acylierungsreaktionen Anwendungen in der Peptidchemie," Chem. Ber. 118:468-482.
Efimov, V.A. et al. (1998). "Synthesis of DNA Analogues with Novel Carboxamidomethyl Phosphonamide and Glycinamide internucleoside Linkages," Bioorganic & Medicinal Chemistry Letters 8:1013-1018.
Eisenberg, E. J. et al. (Apr.-Jul. 2001). "Metabolism of GA-7340, A Novel Phenyl Monophosphoramidate Intracellular Prodrug of PMPA, in Blood," Nucleosides, Nucleotides and Nucleic Acids, 20(4-7):1091-1098.
Esposito, D. et al. (1999). "HIV Integrase Structure and Function," Advances in Virus Research 52:319-333.
Eurasian Office Action mailed on Aug. 24, 2011, for Eurasian Patent Application No. 200700363 filed Jul. 26, 2005, 2 pages.
European Communication mailed on Jul. 2, 2010, for European Patent Application No. 04750807.2 filed on Apr. 26, 2004, 3 pages.
European Communication mailed on Jul. 8, 2009, for European Patent Application No. 04750807.2 filed on Apr. 26, 2004, 6 pages.
European Communication mailed on Mar. 16, 2007, for European Patent Application No. 04750807.2 filed on Apr. 26, 2004, 6 pages.
European Communication mailed on May 7, 2008, for European Patent Application No. 04750807.2 filed on Apr. 26, 2004, 5 pages.
European Notice of Allowance mailed on Nov. 11, 2010, for European Patent Application No. 04750807.2 filed on Apr. 26, 2004, 4 pages.
European Office Action mailed on Mar. 8, 2011, for European Patent Application No. 09790117.7, filed Jul. 7, 2009, 2 pages.
European Search Report mailed on Mar. 12, 2007, for European Patent Application No. 04750807.2 filed on Apr. 26, 2004, 4 pages.
European Search Report mailed on Nov. 2, 2010, for European Patent Application No. 10178348.8 filed on Jul. 26, 2005, 9 pages.
Evans, G.B. (Jul. 17, 2003). "Exploring Structure-Activity Relationships of Transition State Analogues of Human Purine Nucleoside Phosphorylase," J. Med. Chem. 46(15):3412-3423.
Extended European Search Report mailed on Jul. 19, 2011, for European Patent Application No. 10184722.6 filed on Apr. 26, 2004, 11 pages.
Farquhar, D. et al. (1983) "Biologically Reversible Phosphate-Protective Groups," J. Pharm. Sci. 72:324-325.
Frankel, A. et al. (1998). "HIV-1 Fifteen Proteins and an RNA," Annu. Rev. Biochem. 67:1-25.
Freeman, S. et al. (1997). "3 Prodrug Design for Phosphates and Phosphonates," Progress in Medicinal Chemistry 34:112-147.
Galeotti, N. et al. (1996). "A Straightforward Synthesis of Alpha-Amino Phosphonate Monoesters Using BroP or TPyClU," Tetrahedron Letters 37(23):3997-3998.
Gobec, S. et al. (Jul. 5, 2004). "Phosphonate inhibitors of Antiget 85C, a Crucial Enzyme Involved in the Biosynthesis of the Mycobacterium Tuberculosis Cell Wall," Bioorganic and Medicinal Chemistry Letters 14(13):3559-3562.
Griffin, B. et al. (1956). "D-Glucopyranose 6-Deoxy-6-phosphonic Acid," J. Am. Chem. Society 78(10):2336-2338.
Gumina, G. et al. (2001). "Advances in Antiviral Agents for Hepatitis B Virus," Antiviral Chemistry & Chemotherapy 12(Suppl. 1):93-117.
Hakimelahi, G. et al. (1995). "Design, Synthesis, and Structure-Activity Relationship of Novel Dinucleotide Analogs as Agents Against Herpes and Human," J. Med. Chem. 38:4648-4659.
Hanaoka, K. et al. (Jul. 19, 1999). "Antitumor Activity and Novel DNA-Self-Strand-Breaking Mechanism of CNDAC (1-(2-C-Cyano-2-Deoxy-.beta.-D-Arabino-Pentofuranosyl) Cytosine) and its N4-Palmitoyl Derivative (CS-682)," Int. J. Cancer 82(2):226-236.
Hansen, J. et al. (1982). "Partially Protected Polyamines," Synthesis 404-405.
Hartmann, K. et al. (Sep. 1997). "Toxicity Associated With High Dosage 9-[(2R,5R-2,5-Dihydro-5-Phosphonomethoxy)-2-Furanyl]adenine Therapy Off Attempts to Abort Early FIV Infection," Antiviral Res. 36(1):11-25.
Hegedus, L.S. et al. (Nov. 26, 2004). "Synthesis of 4'-Methyl and 4'-cyano Carbocyclic 2',3'-Didehydro Nucleoside Analogues Via 1,4-Addition to Substituted Cyclopentenones," J. Org. Chem. 69(24):8492-8495.
Herczegh, P. et al. (May 23, 2002). "Osteoadsorptive Bisphosphonate Derivatives of Fluoroquinolone Antibacterials," J. Med. Chem. 45(11):2338-2341.
Herdewijn, P. et al. (1987). "3'-Substituted 2', 3'-Dideoxynucleoside Analogues as Potential Anti-HIV (HTLV-III/LAV) Agents," J. Med. Chem. 30:1270-1278.
Hildebrand, C. et al. (1992). "Sodium Salt Glycosylation in the Synthesis of Purine 2'-Deoxyribonucleosides; Studies of Isomer Distribution," J. Org. Chem. 57:1808-1813.
Hirabayashi, H. et al. (2003). "Bone-Specific Drug Delivery Systems: Approaches Via Chemical Modification of Bone-Seeking Agents," Clinical Pharmacokinet. 42(15):1319-1330.
Holy, A. et al. (1989). "Synthesis ofN-(2-Phosphonylmethoxyethyl) Derivatives of Heterocyclic Bases" Collect. Czech. Chem. Commun. 54: 2190-2210.
Hostetler. (1997). "Nucleotides for Topical Treatment of Psoriasis," CAS 127:185859, 2 pages (Chemical abstract).
Hottiger, M. et al. (1996). "Human Immunodeficiency Virus Type 1 Reverse Transcriptase," Biol. Chem. 377:97-120.
Howell, H. et al. (1988). "Antiviral Nucleosides, A Stereospecific, Total Synthesis of 2'-Fluoro-2'-deoxy-beta-D-Arabinoturanosyl Nucleosides," J. Org. Chem. 53:85-88.
Indian Office Action mailed on Jan. 12, 2012, for Indian Patent Application No. 1211/DELNP/2007, filed Jul. 27, 2005, 5 pages.
International Preliminary Report on Patentability mailed on Jan. 20, 2011, for PCT Patent Application No. PCT/US2009/049838, filed on Jul. 7, 2009, 7 pages.

(56) References Cited

OTHER PUBLICATIONS

International Preliminary Report on Patentability mailed on Jan. 30, 2007, for PCT Patent Application No. PCT/US2005/026504, filed on Jul. 26, 2005, 11 pages.
International Search Report and the Written Opinion mailed on Oct. 30, 2006, for PCT Patent Application No. PCT/US2005/026504, filed on Jul. 26, 2005, 18 pages.
International Search Report and Written Opinion mailed on Sep. 25, 2006 for PCT Patent Application No. PCT/US2005/027088, filed on Jul. 27, 2005, 21 pages.
International Search Report mailed on Apr. 13, 2005, for PCT Patent Application No. PCT/US2004/013063 filed on Apr. 26, 2004, 8 pages.
International Search Report mailed on Oct. 8, 2009, for PCT Patent Application No. PCT/US2009/049838, filed on Jul. 7, 2009, 3 pages.
Israeli Official Notification mailed on Jan. 26, 2011, for Israeli Patent Application No. 180758, filed Jul. 27, 2005, 3 pages.
Israeli Official Notification mailed on May 5, 2012, for Israeli Patent Application No. 210006, filed Jul. 7, 2009.
Jacob III, P. (1982). "Resolution of (Racemic)-5-Bromonornicotine. Synthesis of (R)-and (S)-Nornicotine of High Enantiomeric Purity," *J. Org. Chem.* 47:4165-4167.
Jahne, G. et al. (1992). "Preparation of Carbocyclic Phosphonate Nucleosides," *Tetrahedron Letters* 33(37):5335-5338.
Jain, J. et al. (Sep. 2002). "Characterization of Pharmacological Efficacy of VX-148, a New, Potent Immunosuppressive Inosine 5'-Monophosphate Dehydrogenase Inhibitor," Journal of Pharmacology and Experimental Therapeutics 302(3):1272-1277.
Japanese Office Action mailed on Dec. 18, 2013, for Japanese Patent Application No. 2011-517525, filed Jul. 7, 2009, 4 pages.
Japanese Office Action mailed on Dec. 3, 2010, for Japanese Patent Application No. 2007-523866, filed Jul. 27, 2005, 2 pages.
Jeong, L.S. et al. (Jan. 16, 2003). "Design, Synthesis, and Biological Evaluation of Fluoroneplanocin A as the Novel Mechanism-Based Inhibitor of S-Adenosylhomocysteine Hydrolase," J. Med. Chem. 46(2):201-203.
Karpenko, I.L. et al. (Mar. 2003). "Synthesis and Antitherpetic Activity of Acyclovir Phosphonates," Nucleosides, Nucleotides & Nucleic Acids 22(3):319-328.
Kato, K. et al. (1998). "Enantio- and Diastereoselective Syntheis of 4'-a-Substituted Carbocyclic Nucleosides," *Asymmetry* 9:911-914.
Kato, K. et al. (1999). "Stereoselective Synthesis of 4'-..alpha..-Alkycicarbovir Derivatives Based on an Asymmetric Synthesis or Chemo-Enzymatic Procedure," in Chemical & Pharmaceutical Bulletin, Pharmaceutical Society of Japan 49(9):1256-1264.
Katz, R. et al. (1994). "The Retroviral Enzymes," Annu. Rev. Biochem. 63:133-173.
Kazimierczuk, Z. et al. (1984). "Synthesis of 2'-Deoxytubercidin, 2'-Deoxyadenosine, and Related 2'-Deoxynucleosides via a Novel Direct Stereospecific Sodium Salt Glycosylation Procedure," *J. Am. Chem. Soc.* 106:6379-6382.
Khamnei, S. et al. (1996). "Neighboring Group Catalysis in the Design of Nucleotide Prodrugs," J. Med. Chem. 39:4109-4115.
Khandazhinskaya, A.L. et al. (2002). "Carbocyclic Dinucleoside Polyphosphonates: Interactions with HIV Reverse Transcriptase and Antiviral Activity," J. Med. Chem. 45:1284-1291.
Kilpatrick, J.M. et al. (Apr. 2003). "Intravenous and Oral Pharmacokinetic Study of BCX-1777, a Novel Purine Nucleoside Phosphorylase Transition-State Inhibitor, In Vivo Effects on Blood 2'-Deoxyguanosine in Primates," InternationalImmunopharmacology 3(4):541-548.
Kim, C.U.N. et al. (1991). "Regiospecific and Highly Stereoselective Electrophilic Addition to Furanoid Glycals: Synthesis of Phosphonate Nucleotide Analogues with Potent Activity against HIV," J. Org. Chem. 56(8):2642-2647.
Kinsky, S.C. et al. (Feb. 14, 1987). "Inhibition of Cell Proliferation by Putative Metabolites and Nondegradable Analogs of Methotrexate-.gamma.-Dimyristoylphosphatidylethanolamine," Biochimica et Biophysica Acta 917(2):211-218.

Kinsky, S.C. et al. (Feb. 21, 1986). "Effect of Liposomes Sentitized with Methotrexate-.gamma.-Dimyristoylphosphatidylethanolamine on Cells that are Resistant to Methotrexate," Biochimica et Biophysica Acta 885(2):129-135.
Kinsky, S.C. et al. (Sep. 4, 1987). "Circumvention of the Methotrexate Transport System by Methotrexate-Phosphatidylethanolamine Derivatives Effect of Fatty Acid Chain Length," Biochimica et Biophysica Acta 921(1):96-103.
Ko, O.H. et al. (2002). "Efficient Synthesis of Novel Carbocyclic Nucleosides Via Sequential Claisen Rearrangement and Ring-Closing Metathesis," Tetrahedron Letters 43: 6399-6402.
Kojima, T. et al. (Apr. 2006). "Crystalline Form Information From Multiwell Plate Salt Screening by Use of Raman Microscopy," Pharm. Res. 23(4):806-812.
Konakahara, T. et al. (Jan. 1993). "A Convenient Method for the Synthesis of Activated N-Methylcarbamates," Synthesis 103-106.
Krayevsky, A.A. et al. (1992). "5'Hydrogenphosphonates and 5'-Methylphosphonates of Sugarmodified Pyrimidine Nucleosides as Potential Anti-HIV-I Agents", Nucleosides, Nucleotides & Nucleic Acids 11(2-4):177-196.
Krowczy ski, L. (1977). "Excipients for Manufacturing of Drug Forms," Chapter 4 in Outline of Drug Form Technology: A Textbook for Pharmacy Students, 3.sup.rd Edition.
Krowczy ski, L. (1982). "Drug Interaction," Chapter 17 in Outline of Clinical Pharmacy, pp. 323-342.
Kumamoto, H. et al. (May 31, 2002). "Simple Entry to 3'-Substituted Analogues of Anti-HIV Agent Stavudine Based on an Anionic O—> C Stannyl Migration," J. Org. Chem. 67(11):3541-3547.
Kunz, H. et al. (1985). "71. Synthesis of the Glycopeptide Partial Sequence A.sup.80-A.sup.84 of Human Fibroblast Interferon," Helvetica Chimica Acta 68:618-622.
Lee, K. et al. (Apr. 8, 1999). "Synthesis and Anti-HIV and Anti-HBV Activities of 2'-Fluoro-2',3'-Unsaturated L-Nucleosides," J. Med. Chem. 42(7):1320-1328.
Lee, K. et al.(Mar. 14, 2002). "Structure-Activity Relationships of 2'-Fiuoro-2',3'-unsaturated D-Nucleosides as Anti-HIV-1 Agents," J. Med. Chem. 45(6):1313-1320.
Lee, S. et al. (2002). "Large-Scale Aspects of Salt Formation: Processing of Intermediates and Final Products," Chapter 8 in *Handbook of Pharmaceutical Salts: Properties, Selection, and Use*, pp. 191-220.
Leff et al. (2002). "Antidiabetic PPAR-.gamma.. Ligands: An Update on Compunds in Development," Curr. Med. Chem. Imun. Endoc. & Metab. Agents 2(1):33-47.
Lewandowicz, A. et al. (Aug. 22, 2003). "Achieving the Ultimate Physiological Goal in Transition State Analogue Inhibitors for Purine Nucleoside Phosphorylase," The Journal of Biological Chemistry 278(34):31465-31468.
Lochmuller, C.H. et al. (1975). "Chromatographic Resolution of Enantiomers Selective Review," Journal of Chromatography 113:283-302.
Lu, X. et al. (1987). "Palladium-Catalyzed Reaction of Aryl Polyfluoroalkanesulfonates with O, O-Dialkyl Phosphonates," *Synthesis* 726-727.
Ma, T. et al. (1997). "Synthesis and Anti-Hepatitis B Virus Activity of 9-(2-Deoxy-2-fluoro-Beta-L-arabinofuranosyl)purine Nucleosides," J. Med. Chem. 40:2750-2754.
Mackman et al. (2010). "Discovery of GS-9131: Design, Synthesis and Optimization of Amidate Prodrugs of the Novel Nucleoside Phosphonate HIV Reverse Transcriptase (RT) Inhibitor GS-9148," Bioorganic & Medicinal Chemistry 18:3606-3617.
Maffre-Lafon, D. et al. (1994). "Solid Phase Synthesis of Phosphonopeptides from Fmoc Phoaphonodipeptides," Tetrahedron Letters 35(24):4097-4098.
Margolin et al. (1994). "AMP Deaminase as a Novel Practical Catalyst in the Synthesis of 6-Oxopurine Ribosides and Their Analogs," *Journal of Organic Chemistry* 59(24):7214-7218.
Marquez, V.E. et al. (1990). "Acid-Stable 2'-Fluoro Purine Dideoxynucleosides as Active Agents against HIV," J. Med. Chem. 33:978-985.
Maynard, J. A. et al. (1963). "Organophosphorus Compounds II. Preparation of Phosphonic Acid Esters Using The Dicyclohexylcarbodi-imide Reagent," *Aust. J. Chem.* 16:609-612.

(56) References Cited

OTHER PUBLICATIONS

McKenna, C. et al. (1979). "Functional Selectivity in Phosphonate Ester Dealkylation with Bromotrimethylsilane," J.C.S. Chem. Comm. 739.
Melvin, L.S. (1981). "An Efficient Synthesis of 2-Hydroxyphenylphosphonates," Tetrahedron Letters 22(35):3375-3376.
Menendez-Arias, L. (Aug. 2002). "Targeting HIV: Antiretroviral Therapy and Development of Drug Resistance," Trends in Pharmacological Sciences 23(8):381-388.
Mexican Office Action mailed on Feb. 16, 2012 for Mexican Patent Application No. MX/a/2010/007924 filed on Jul. 27, 2005, 10 pages.
Mexican Office Action mailed on May 22, 2012 for Mexican Patent Application No. MX/a/2011/000306 filed on Jul. 7, 2009, 5 pages.
Mikhailopulo, I.A. et al. (2000). "Pyrophosphoryl Derivatives of 1-(2-Deoxy-3-O-Phosphonomethyl-Beta- and -Alpha-D-erythro-Pentofuranosyl)Thyrnine: Synthesis and Substrate Properties Towards Some DNA Polymerases," Nucleosides, Nucleotides, andNucleic Acids 19(10-12)1885-1909.
Mikhailopulo, I.A. et al. (Jul. 25, 2003). "2'-Chloro-2',3'-Dideoxy-3'-Fluoro-d-Ribonucleosides: Synthesis, Stereospecificity, Some Chemical Transformations, and Conformational Analysis," J. Org. Chem. 68(15):5897-5908.
Mikhailopulo, I.A. et al. (May 12, 1993, e-pub. Jan. 25, 2006). "Synthesis of 2'-Azido-2',3'-Didehydro-2',3'-Dideoxythymidine," Liebigs Annalen der Chemie 5:513-519.
Mitchell, A. et al. (1992). "Bioreversible Protection for the Phospho Group: Bioactivation of the Di(4 acyloxybenzyl) Phosphoesters," J. Chem. Soc. Perkin Trans 1:2345-2353.
Mitsunobu, O. (1981). "The Use of Diethyl Azodicarboxylate and Triphenylphosphine in Synthesis and Transformation of Natural Products," Synthesis 1-28.
Moon, H.R. et al. (2002). "Synthesis of 2',3'-Didehydro-2',3'-Dideoxy-2'-Fluoro Apionnucleosidesas Potential Antiviral Agents," J. Chem. Soc. Perkin Trans. 1:1800-1804.
Morgan, B. et al. (1994). "Structure-Based Design of an Inhibitor of the Zinc Peptidase Thermolysin," *J. Am. Chem. Soc.* 116(8):3251-3260.
Morgans et al. (1995). "5-Substituted Derivatives of Mycophenolic Acid," CAS 124:86709 (Chemical abstract).
Morr, M. at al (2001). "Formation of Phostonic Acids During the Reduction of Azidonucleosidephosphonic Acids," *Tetrahedron Letters* 42:8841-8843.
Muesing, M. et al (Feb. 1985). "Nucleic Acid Structure and Expression of the Human AIDS/Lymphadenopathy Retrovirus," Nature 313(7):450-458.
Musiol, H. et al. (1994). "On the Synthesis of Phosphonamidate Peptides," *J. Org. Chem.* 59(21):6144-6146.
New Zealand Office Action mailed on May 20, 2011, for New Zealand Patent Application No. 590075, filed Jul. 7, 2009, 2 pages.
Notice of Allowance mailed on Mar. 18, 2014, for U.S. Appl. No. 13/848,593, filed Mar. 21, 2013, 7 pages.
Notice of Allowance mailed on Oct. 2, 2014, for U.S. Appl. No. 14/150,677, filed Jan. 8, 2014, 7 pages.
Notice of Allowance mailed on Oct. 8, 2013, for U.S. Appl. No. 12/999,441, filed Jul. 7, 2009, 7 pages.
Office Action dated Jul. 24, 2015 for Canadian Application No. 2,729,769.
Ohashi, K. et al. (1988). "Synthesis of Phosphonosphingoglycolipid Found in Marine Snail *Turbo cornutus,*" *Tetrahedron Letters* 29(10):1189-1192.
Okamoto, Y. et al. (1990). "Optical Resolution of Dlhydropyridine Enantiomers by High-Performance Liquid Chromatography Using Phenylcarbamates," *Journal of Chromatography* 513:375-378.
Ono-Nita, S.K. et al. (Aug. 2002). "Novel Nucleoside Analogue MCC-478 (LY582563) Is Effective against Wild-Type or Lamivudine-Resistant Hepatitis B Virus," Antimicrobial Agents and Chemotherapy 46(8):2602-2605.

Pankiewicz, K.W. (Jan. 31, 2002). "Novel Mycophenolic Adenine Bis(phosphonate) Analogues as Potential Differentiation Agents against Human Leukemia," J. Med. Chem. 45(3):703-712.
Paquet, A. (1982). "Introduction of 9-Fluorenylmethyloxycarbonyl, Trichloroethoxycarbonyl, and Benzyloxycarbonyl Amine Protecting Groups Into O-Unprotected Hydroxyamino Acids Using Succinimidyl Carbonates," Can. J. Chem. 60:976-960.
Parang, K. et al. (Oct. 2000). "Novel Approaches for Designing 5'-0-Ester Prodrugs of 3'-Azido-2', 3'-dideoxythymidine (AZT)," Current Medicinal Chemistry 7(10):995-1039.
Patois, C. et al. (1990). "2-Alkyl-5, 5-Dimethyl-1,3,2-Dioxephosphorinan-2-Ones .alpha.-Lithiated Carbanions. Synthesis, Stability, and Conformation," J. Chem. Soc. Perkin Trans. (1)1577-1581.
Pauwels et al. (1988). "Investigations on the Anti-HIV Activity of 2', 3'-Dideoxyadenosine Analogues with Modifications in Either the Pentose or Purine Moiety," Biochem. Pharmacology 37(7) :1317-1325.
Peruvian Office Action mailed on Jul. 4, 2012, for Peruvian Patent Application No. 6.2011 filed on Jul. 7, 2009, 14 pages.
Petrakis, K. et al. (1987). "Palladium-Catalyzed Substitutions of Triflates Derived from Tyrosine-Containing Peptides and Simpler Hydroxyarenes Forming," J. Am. Chem. Soc. 109:2831-2833.
Polish Office Action mailed on Oct. 22, 2013, for Polish Patent Application No. P382843, filed on Jul. 27, 2005, 1 page.
Polish Office Action mailed on Oct. 5, 2011 for Polish Patent Application No. P382843 filed Jul. 27, 2005, 5 pages.
Porche, D. J. (1999). "State of the Art: Antiretroviral and Prophylactic Treatments in HIV/AIDS," Nursing Clinics of North America 34:95-112.
Prashad, M. et al. (Sep. 20, 2002). "An Efficient and Large-Scale Enantioselective Synthesis of PNP405: A Purine Nucleoside Phosphorylase Inhibitor," J. Org. Chem. 67(19):6612-6617.
Puech, F. et al. (1993). "Intracellular Delivery of Nucleoside Monophosphates through a Reductase-Mediated Activation Process," Antiviral Research 22:155-174.
Pungente, M. et al. (2001). "Synthesis and Stereochemical Elucidation of a 14-Membered Ring Phosphonate," Organic Letters 3(5):643-646.
Quast, H. et al. (1974). "Herstellung Von Methylphosphonsaure-Dichlorid," Synthesis 490.
Ray, A.S. et al. (2008). "Intracellular Metabolism of the Nucleotide Prodrug GS-9131, a Potent Anti-Human Immunodeficiency Virus Agent," Antimicrob. Agents Chemother. 52(2):648-654.
Ray, A.S. et al. (Apr. 2004). Role of Purine Nucleoside Phosphorylase in Interactions between 2', 3'-Dideoxyinosine and Allopurinal, Ganciclovir, or Tenofovir, Antimicrobial Agents and Chemotherapy 48(4):1089-1095.
Redmore, D. (1970). "Phosphorus Derivatives of Nitrogen Heterocycles. 2. Pyridinephosphonic Acid Derivatives," J. Org. Chem. 35(12):4114-4117.
Remington (Jun. 1995). Remington: The Science and Practice of Pharmacy, 19.sup.th Edition, vol. 1, Chapters: 20, 83 and 91.
Roach et al. (1987). "Fluorescence Detection of Alkylphosphonic Acids Using p-(9-Anthroyloxy)phenacyl Bromide," Analytical Chem. 59:1056-1059.
Roberts, S.M. (Dec. 1998). "Development of the Route to the New Anti-AIDS Drug Abacavir: A Highlight of Academic/Industry Laison," IDrugs 1(8):896-899.
Rosenberg, I. et al. (1987). "Synthesis of Potential Prodrugs and Metabolites of 9-(S)-(3-Hydroxy-2-Phosphonylmethoxypropyl) Adenine," Collect. Czech. Chem. Commun. 52:2792-2800.
Rosowsky, A. et al. (Jul. 1988). "Methotrexate Analogues. 32. Chain Extension, .alpha.-Carboxyl Deletion, and .gamma.-Carboxyl Replacement by Sulfonate and Phosphonate: Effect on Enzyme Binding and Cell-Growth Inhibition," J. Med. Chem.31(7):1326-1331.
Rosowsky, A. et al. (Oct. 1, 1986). "Methotrexate Analogues-27. Dual Inhibition of Dihydrofolate Reductase and Folylpolyglutamate Synthetase by Methotrexate and Aminopterin Analogues with a .gamma.-Phosphonate Group in the Side Chain," BiochemicalPharmacology 35(19) :3327-3333.

(56) References Cited

OTHER PUBLICATIONS

Saady, M. et al. (1995) "Selective Monodeprotection of Phosphate, Phosphite, Phosphonate, and Phosphoramide Benzyl Esters," J. Org. Chem. 60:2946-2947.
Sasaki, T. et al. (1971). "Chemistry of Cyanoacetylenes. Part X. Further Studies on the Reactions of Cyano-Ynamines with Hydrogen Halides and Bromine," J. Chem. Soc. C. 18:3056-3060.
Schon, I. et al. (1986) "9-Fluorenylmethyl Pentafluorophenyl Carbonate as a Useful Reagent for the Preparation of N-9-Fluorenylmethyloxycarbonylamino," Synthesis 303-305.
Schultz, C. C (Mar. 20, 2003). "Prodrugs of Biologically Active Phosphate Esters," Bioorganic & Medicinal Chemistry 11(6):885-898.
Sekiya, K. et al. (Jul. 4, 2002). "2-Amino-6-arylthio-9-[2-(phosphonomethoxy) ethyl] purine Bis(2,2,2-Trifluoroethyl) Esters as Novel HBV-Specific Antiviral Reagents," Journal of Medicinal Chemistry 45(14):3138-3142.
Serafinowska, H. et al. (1995). "Synthesis and in Vivo Evaluation of Prodrugs of 9-[2-(Phosphonomethoxy)ethoxy]adenine," J. Med. Chem. 38:1372-1379.
Sharma, S. et al. (1989). "Spermexatin and Spermaxatol: New Synthetic Spermidine-Based Siderophore Analogues," J. Med. Chem. 32:357-367.
Shi, W. et al. (Apr. 30, 2004, e-pub. Feb. 23, 2004). "Plasmodium Falciparum Purine Nucleoside Phosphorylase: Crystal Structures, Immucillin Inhibitors, and Dual Catalytic Function," Journal of Biological Chemistry 279(18)18103-18106.
Shirokova, E. A. (2003). "New Lipophilic Derivatives of AZT and d4T 5'-Phosphonates," Nucleosides, Nucleotides and Nucleic Acids, 22(5-8):981-985.
Siddiqui, A. Q. et al. (Feb. 11, 1999). "The Presence of Substituents on the Aryl Moiety of the Aryl Phosphoramidate Derivative of D4T Enhances Anti-HIV Efficacy in Cell Culture: A Structure Activity Relationship," J. Med. Chem. 42(3):393-399.
Silverberg, L. et al. (1996). "A Simple, Rapid and Efficient Protocol for the Selective Phosphorylation of Phenols with Dibenzyl Phosphite," Tetrahedron Letters 37(6):771-774.
Sintchak, M.D. et al. (May 2000). "The Structure of Inosine 5'-Monophosphate Dehydrogenase and the Design of Novel Inhibitors," Immunopharmacology 47(2-3):163-184.
Smith, M. et al. (1994). "Development and Significance of Nucleoside Drug Resistance in Infection Caused by the Human Immunodeficiency Virus Type 1," Clin. Invest. Med. 17(3):226-243.
Smith, R. et al. (2003). "A Novel MyD-1 (S1RP-1) Signaling Pathway that Inhibits LPS-Induced TNF Production by Monocytes," Blood 102(7):2532-2540.
Squires, K.E. (2001). "An Introduction to Nucleoside and Nucleotide Analogues," Antiviral Therapy 6(Suppl.3):1-14.
Srinivas, R.V. et al. (1993). "Metabolism and In Vitro Antiretroviral Activities of Bis(Pivaloyloxymethyl) Prodrugs of Acyclic Nucleoside Phosphonates," Antimicrobial Agents and Chemotherapy 37(10): 2247-2250.
Stahl, P.H. (2002). "Appendix," in Handbook of Pharmaceutical Salts: Properties, Selection, and Use, pp. 329-350.
Stahl, P.H. et al. (2002). "Control of the Crystallization Process," Chapter 5 in Handbook of Pharmaceutical Salts: Properties, Selection, and Use, pp. 214 and 254-255.
Stahl, P.H. et al. (2002). "Monographs on Acids and Bases," Chapter 12 in Handbook of Pharmaceutical Salts: Proierties Selection and Use, pp. 265-327.
Stamm, H. et al. (1980). "Reactions with Aziridines XXI The (Michaelis-) Arbuson Reaction with N-Acyl Aziridines and Other Amidoethylations at Phosphorus," Tetrahedron Letters 21:1623-1626.
Sturtz et al. (1984). "Amethopterine (methotrexate) Phosphonoglutamic Acid Analogs. Part II. Dihydrofolate Reductase Inhinition," CAS 101:143560 (Chemical abstract).
Sturtz, G. et al. (1984). "Analogues Phosphonoglutamiques D'amethopterine (methotrexate)," Eur. J. Med. Chem. 19(3):267-273 (English summary available).
Sturtz, G. et al. (1990). "Su rune nouvelle approche de pharmacomodulation du methotrexate: synthese d'analogues gem-diphosphoniques d'amethopterine et de la N-10 deaza amethopterine," in Medicinal Chemistry, C. R. Academie des Sciences, Paris,10(2):739-742. (English abstract available).
Sturtz, G. et al. (1992). "A Study of the Delivery-Targeting Concept Applied to Antineoplasic Drugs Active on Human Osteosarcoma, I. Synthesis and Biological Activity in Nude Mice Carrying Human Osteosarcoma Xenografts of Gem-BisphosphonicMethotrexate Analogues," Eur J. Med. Chem. 27(8):825-833.
Sturtz, G. et al.(1993). "Synthesis of Gem-Bisphosphonic Methotrexate Conjugates and their Biological Response Towards Walker's Osteosarcoma," Eur. J. Med. Chem. 28:899-903.
Sun, C. et al. (2002). "A General Synthesis of Diozolenone Prodrug Moieties," Tetrahedron Letters 43:1161-1164.
Szabo, T. et al. (1995). "Solid Phase Synthesis of 5'-Methylenephosphonate DNA" Nucls. & Nucli. 14(3-5):871-874.
Taiwanese Office Action mailed on Jul. 8, 2011, for Taiwanese Patent Application No. 094125503.
Tang, T. et al. (1999). "The Tert-Butanesulfinyl Group: An Ideal Chiral Directing Group and Boc-Surrogate for the Asymmetric Synthesis and Applications of .beta.-Amino Acids," J. Org. Chem. 64:12-13.
Tarrago-Litvak, L. et al. (1994). "The Reverse Transcriptase of HIV-1: From Enzymology to Therapeutic Intervention," The FASEB Journal 8:497-503.
Thomson, W. et al. (1993). "Synthesis and Bioactivation of Bis(aroyloxymethyl) and Mono(aroyloxymethyl) Esters of Benzylphosphonate," J. Chem. Soc. Perkin Trans. 19:2303-2308.
Toyota, A. et al. (Jun. 25, 1998). ".alpha.-Fluorination of 6-Phenylsulfinyl-2-Azabicyclo[2.2.1]heptan-3-One and Synthesis of 2'-Fluoro Substituted Carbovir," Tetrahedron Letters 39(26):4687-4690.
Truvada.RTM. Label Revision Approved on Jul. 16, 2012, NDA No. 021752, Reference ID 3159758, 38 pages.
U.S. Final Office Action mailed on Dec. 15, 2011, for U.S. Appl. No. 11/658,628, filed Sep. 25, 2012, 6 pages.
U.S. Final Office Action mailed on Mar. 28, 2013, for U.S. Appl. No. 12/999,441, filed Jul. 7, 2009, 16 pages.
U.S. Non-Final Office Action mailed on Apr. 28, 2011, for U.S. Appl. No. 11/658,628, filed Sep. 25, 2012, 12 pages.
U.S. Non-Final Office Action mailed on Aug. 28, 2012, for U.S. Appl. No. 12/999,441, filed Jul. 7, 2009, 16 pages.
U.S. Non-Final Office Action mailed on Dec. 5, 2014, for U.S. Appl. No. 14/309,790, filed Jun. 19, 2014, 6 pages.
U.S. Non-Final Office Action mailed on Feb. 27, 2014, for U.S. Appl. No. 13/653,982, filed Oct. 17, 2012, 6 pages.
U.S. Non-Final Office Action mailed on Jun. 20, 2014, for U.S. Appl. No. 14/150,677, filed Jan. 8, 2014, 5 pages.
U.S. Non-Final Office Action mailed on Nov. 6, 2014, for U.S. Appl. No. 13/653,982, filed Oct. 17, 2012, 5 pages.
U.S. Non-Final Office Action mailed on Oct. 8, 2014, for U.S. Appl. No. 14/178,237, filed Feb. 11, 2014, 4 pages.
U.S. Non-Final Office Action mailed on Oct. 9, 2013, for U.S. Appl. No. 13/848,593, filed Mar. 21, 2013, 7 pages.
U.S. Non-Final Office Action mailed on Sep. 24, 2012, for U.S. Appl. No. 13/187,293, filed Jul. 20, 2011, 7 pages.
Van Der Laan, A.C. et al. (1996). "An Approach Towards the Synthesis of Oligomers Containing a N-2 Hydroxyethyl-aminomethylphosphonate Backbone: A Novel PNA Analogue," Tetrahedron Letters 37(43):7857-7860.
Van Der Laan, A.C. et al. (1998). "Optimization of the Binding Properties of PNA-(5')-DNA Chimerae," Bioorg. Med. Chem. Letters 8:663-668.
Vieira De Almeida, M. et al. (1999). "Synthesis of Deoxy Phosphatidylinositol Analogues and Phosphonate Isosters of Ins(1,4,5)P3," Tetrahedron Letters 55:12997-13010.
Vielhaber, B. (2000). "Bericht Vom 3rd International Workshop on Salvage Therapy for HIV Infection," in Deutsche Aids-Hilfe e.V. FaxReport zu HIV and AIDS pp. 12-14.
Vietnamese Office Action mailed on Jul. 5, 2011, for Vietnamese Patent Application No. 1-2011-00030, filed Jul. 7, 2009, 2 pages.

(56) References Cited

OTHER PUBLICATIONS

Vietnamese Office Action mailed on Mar. 14, 2011, for Vietnamese Patent Application No. 1-2011-00030, filed on Jul. 7, 2009, 1 page.
Von Der Helm, K. (1996). "Retroviral Proteases: Structure, Function and Inhibition From a Non-Anticipated Viral Enzyme to the Target of a Most Promising HIV Therapy," Biol. Chem. 377:765-774.
Waegell W. et al. (2002). "A420983, a Novel, Small Molecule Inhibitor of LCK Prevents Allograft Rejection," Transplantation Proceedings 34:1411-1417.
Watanabe, Y. et al. (1988). "Dibenzyl Phosphorofluoridate, A New Phosphorylating Agent," Tetrahedron Letters 29(45):5763-5764.
Wermuth, C.G. et al. (2002). "Selected Procedures for the Preparation of Pharmeaceutically Acceptable Salts," Chapter 11 in Handbook of Pharmaceutical Salts: Properties, Selection, and Use, pp. 249-263.
Wessig, P. et al. (1997). "A Convenient One-Pot Conversion of N-Boc-.beta.-Aminoalcohols into N-Boc-Aziridines," Synlett 8:893-894.
West. (1984). "Solid-State Chemistry and its Application," John Wiley & Sons, 3 pages.
Wissner, A. et al. (1992). "Analogues of Platelet Activating Factor. 6 Mono- and Bis-Aryt Phosphate Antagonists of Platelet Activating Factor," J. Med. Chem. 35:1650-1662.
Woltermann, C.J. et al. (Apr. 5, 2004). "A Stereoselective Synthesis of 9-(3-O-benzyl-5-O-Tetrahydropyranyl-.beta.-D-Arabinofuranosyl)Adenine, a Potentially Useful Intermediate for Ribonucleoside Synthesis," Tetrahedron 60(15):3445-3449.
Written Opinion of the International Searching Authority mailed on Apr. 13, 2005, for PCT Patent Application No. PCT/US2004/013063 filed on Apr. 26, 2004, 8 pages.
Written Opinion of the International Searching Authority mailed on Oct. 8, 2009, for PCT Patent Application No. PCT/US2009/049838 filed on Jul. 7, 2009, 5 pages.
Wroblewski, A. et al. (2004). "Synthesis of (1 R,2S)- and (1 S,2S)-3-(4-Carbamoyl-1,2,3-Triazol-1-yl)-1,2-Dihydroxypropylphosphonates," Tetrahedron: Asymmetry 15:1457-1464.
Yamada, K. et al. (2002). "Reactions of 1-Methoxy-3-(2-nitrovinyl)indole with Nucleophiles: An Interesting Solvent Effect and a Novel Preparation of 3-Substituted 1-Methoxyindoles," Heterocycles 57(7):1231-1234.
Yamauchi, K. et al. (1984). "Synthesis of Peptides Analogues Containing (2- Aminoethyl)phosphonic Acid(ciliatine)," J. Org. Chem. 49(7):1158-1163.
Zemlicka, J. et al. (1972). "Nucleosides, XV. Decarboxylative Elimination of 2'-Deoxynudeodise Uronic Acids," J. Am. Chem. Soc. 94(9):3213-3218.
Zhou, W. et al. (Jun. 17, 2004). "Synthesis, Structure-Activity Relationships, and Drug Resistance of Beta-D-3'-Fluoro-2', 3'-Unsaturated Nucleosides as Anti-HIV Agents," J. Med. Chem. 47(13):3399-3408.
Cihlar et al. (2009)"Novel Nucleotide Human Immunodeficiency Virus Reverse Transcriptase Inhibitor GS-9148 With a Low Nephrotoxic Potential: Characterization of Renal Transport and Accumulation". *Antimicrob Agents Chemother*; 53(1):150-6.

\* cited by examiner

SALTS OF HIV INHIBITOR COMPOUNDS

CROSS REFERENCE TO RELATED APPLICATIONS

This patent application is a continuation of U.S. patent application Ser. No. 14/585,011, filed Dec. 29, 2014, now U.S. Pat. No. 9,381,206, which is a continuation of U.S. patent application Ser. No. 14/150,677, filed Jan. 8, 2014, now U.S. Pat. No. 8,951,986, which is a continuation of U.S. patent application Ser. No. 12/999,441, filed Dec. 16, 2010, now U.S. Pat. No. 8,658,617, which is a national stage filing under 35 U.S.C. §371 of International Patent Application No. PCT/US2009/049838, filed on Jul. 7, 2009, which claims the benefit of priority of U.S. Provisional Patent Application Ser. No. 61/078,989, filed Jul. 8, 2008. The contents of each application is incorporated by reference.

FIELD OF THE INVENTION

The invention relates generally to salts of compounds with antiviral activity and more specifically with anti-HIV properties.

BACKGROUND OF THE INVENTION

Human immunodeficiency virus (HIV) is a retrovirus that can lead to acquired immunodeficiency syndrome (AIDS), a condition in humans in which the immune system is weakened, leading to life-threatening opportunistic infections. Inhibitors of HIV are useful to treat HIV infection in a mammal (e.g., reduce and limit the establishment and progression of infection by HIV) as well as in diagnostic assays for HIV. The usefulness of currently marketed inhibitors of HIV is to some extent limited by toxicity and other side effects. Thus, there is a need for new HIV therapeutic agents.

A pharmaceutical formulation of a therapeutic agent must reproducibly and consistently deliver the therapeutic agent to a patient in need thereof. This consistency of delivery can be achieved, at least in part, by incorporation of a stable, soluble, solid-state form of the therapeutic agent into the pharmaceutical composition. Moreover, the synthesis of the desired solid-state form of the therapeutic agent should be technically and economoically feasible, and should be suitable for full-scale commercial production.

SUMMARY OF THE INVENTION

Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a reverse transcriptase inhibitor that blocks the replication of HIV viruses, in vivo and in vitro, and has limited undesirable side effects when administered to human beings. The structure of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is shown in Formula P:

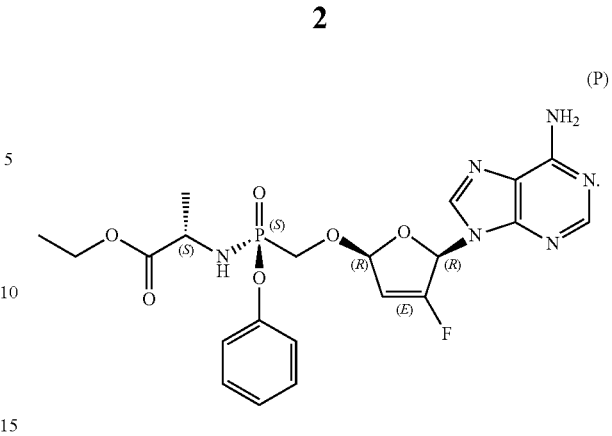

Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a low melting point, amorphous, solid which is difficult to isolate, purify, store for an extended period, and formulate as a pharmaceutical composition. Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is also a weak base that is capable of forming salts with acids. Accordingly, in one aspect, the present invention provides stable salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate that are more physically stable, and are more readily isolated and formulated, than the free base form of the compound.

The salts of the present invention are useful, for example, for treating human patients infected with human immunodeficiency virus (strains of HIV-1 or HIV-2) which causes AIDS. The salts of the present invention are also useful, for example, for preparing a medicament for treating HIV or an HIV associated disorder. The salts of the present invention are also useful, for example, for inhibiting the replication of HIV viruses in vitro, and can be used, therefore, in biological assays as a control compound for identifying other reverse transcriptase inhibitors, or for investigating the mechanism of action of HIV reverse transcriptase and its inhibition.

Thus, in one aspect, the present invention provides citrate, succinate and malonate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate, and methods of making the foregoing salts. In some embodiments, the salts of the present invention are anhydrous, while in other embodiments the salts of the present invention are at least partially hydrated. In some embodiments, the salts of the present invention exist as crystalline forms.

Thus, the present invention comprises citrate, succinate and malonate salts of the compound of Formula P, as well as hydrates thereof. The inventive hydrates may be in a partial (e.g., hemi-hydrate) or full hydrated state (e.g., monohydrate). The present invention also comprises the subject salts in anhydrous or essentially anhydrous states. Similarly, the inventive salts and hydrates thereof comprise amorphous and crystalline states, as well as states comprising both amorphous and crystalline characteristics. As used herein, "crystalline" means a material that has an ordered, long range molecular structure. In contrast, "amorphous" materials do not possess long range order. It is understood that crystalline materials are generally more stable thermodynamically than amorphous forms of the same substance. Thus, with only a few notable exceptions, it is generally preferred to use crystalline materials in pharmaceutical applications. A measure of the degree of crystallinity of the inventive compounds can be seen, for example, in the sharpness of the DSC and XRPD absorption bands (peaks). The sharper the peak, the higher the degree of crystallinity. Conversely, the broader the peak, the lower the degree of crystallinity.

As described more fully in Example 12 herein, in specific embodiments, a citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is characterized by absorption bands, obtained from an X-ray powder diffraction pattern, at spectral d-spacings of 4.48, 3.12 and 6.05 angstroms; a succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is characterized by absorption bands, obtained from an X-ray powder diffraction pattern, at spectral d-spacings of 3.57, 4.80 and 4.99 angstroms; and a malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is characterized by absorption bands, obtained from X-ray powder diffraction pattern, at spectral d-spacings of 4.99, 5.93 and 4.72 angstroms. In another specific embodiment, the present invention provides a citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate having a melting point of from 142° C. to 150° C.

Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is an amidate prodrug which undergoes reaction with and decomposition in protic solvents. The rate of the reaction depends on pH and temperature. Consequently, the formation of a stable salt between the amidate prodrug and citric acid, succinic acid and/or malonic acid, which each contain nucleophilic moieties capable of reacting with the prodrug (e.g., reaction with the amidate moiety of the prodrug) is a surprising and unexpected result.

In another aspect, the present invention provides pharmaceutical compositions that each include a therapeutically effective amount of a salt of the present invention and a pharmaceutically acceptable carrier or excipient. Pharmaceutical compositions of the present invention may also include an additional therapeutic agent, such as an antiviral, antibacterial, antifungal or anticancer agent. The pharmaceutical compositions of the invention may be in the form of unit dosage forms, such as tablets or capsules. The unit dosage forms typically provide an effective daily dose of a salt of the present invention to a human being in need thereof. Effective daily doses of the salts of the present invention are typically from 1 mg to 100 mg, such as from 10 mg to 30 mg.

In another aspect, the present invention provides methods of making the citrate, succinate and malonate salts of the present invention. Thus, for example, the present invention provides a process for preparing a citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate, wherein the process includes the step of contacting about one equivalent of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate free base in a suitable solvent (e.g., acetonitrile) with form about one equivalent to about 1.2 equivalents of citric acid at a temperature in the range of from about 55° C. to about 75° C.

The present invention also provides a process for preparing a succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate, wherein the process includes the step of contacting about one equivalent of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate free base in a suitable solvent (e.g., 2-butanone) with from about one equivalent to about 1.2 equivalents of succinic acid at a temperature in the range of from about 60° C. to about 70° C. to form the succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

Further, the present invention provides a process for preparing a malonate salt of Ethyl N—[(S)({[(2R,5R)-5-(6-amino-9H-purin-9-yl)-4-fluoro-2,5-dihydrofuran-2-yl]oxy}methyl) phenoxyphosphinoyl]-L-alaninate, wherein the process includes the step of contacting about one equivalent of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate free base in a suitable solvent (e.g., 2-butanone) with from about one equivalent to about 1.2 equivalents of malonic acid at a temperature in the range of from about 50° C. to about 70° C. to form the malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

In a further aspect, the present invention provides methods of treating or prophylactically preventing AIDS, wherein the methods include the step of administering to a human being suffering from AIDS a therapeutically effective amount of a salt of the invention, or a hydrate thereof.

DETAILED DESCRIPTION OF EXEMPLARY EMBODIMENTS

Figure 1:
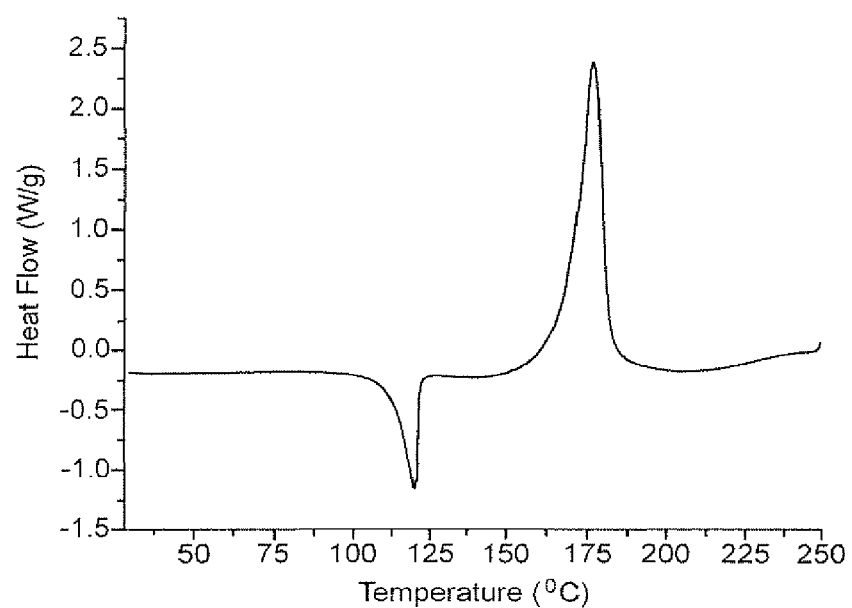
FIG. 1 shows a characteristic differential scanning calorimetry (DSC) trace for the malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

When tradenames are used herein, applicants intend to independently include the tradename product and the active pharmaceutical ingredient(s) of the tradename product.

Salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate In one aspect, the present invention provides citrate, succinate and malonate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

The citrate salt is shown in Formula I:

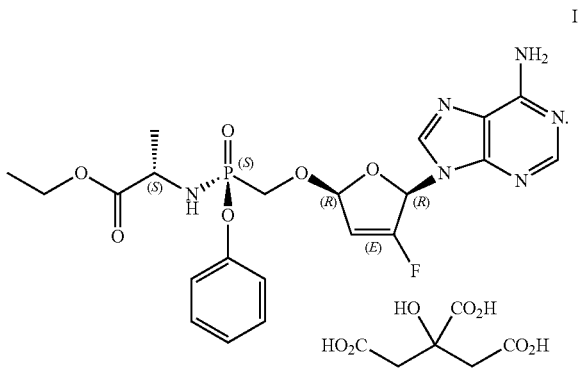

I

The succinate salt is shown in Formula II:

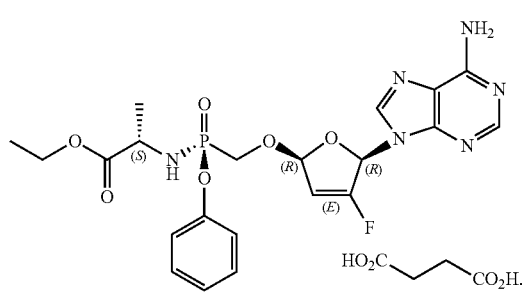

II

The malonate salt is shown in Formula III:

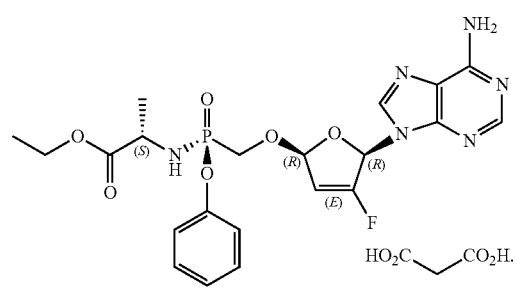

III

A method for synthesizing Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is described in Example 1 herein. Methods for making the malonate, succinate and citrate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate are described in Examples 3, 4 and 5, respectively, herein. Some physical properties of the foregoing salts are described in Example 6 herein and demonstrate, for example, that each of these salts is physically stable when stored at 40° C. and a relative humidity of 75%.

The citrate, succinate and malonate salts of Ethyl N—[(S)({[(2R,5R)-5-(6-amino-9H-purin-9-yl)-4-fluoro-2,5-dihydrofuran-2 yl]oxy}methyl)phenoxyphosphinoyl]-L-alaninate are useful, for example, for inhibiting the replication of HIV in vitro and in vivo. In this regard, as explained more fully in Example 8 herein, Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a prodrug that is metabolized in the human body to yield a parent compound which, in turn, is phosphorylated within the body to produce the active metabolite that inhibits HIV replication. Example 8 herein shows that Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate causes a greater accumulation of the active metabolite in white blood cells, which are the cells that harbor the HIV virus, than does the parent compound. Further, Example 9 herein presents in vitro data showing that Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a more potent anti-HIV drug than the parent compound as assessed in an in vitro assay. Additionally, Example 10 herein provides data showing that a tablet containing the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate provides this drug to the bloodstream of Beagle dogs with similar pharmacokinetics to a liquid preparation of the drug administered orally. Thus, the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a physically and chemically stable composition of matter that can be administered orally to a living subject, to provide a therapeutically effective amount of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate, which is a more effective anti-HIV agent than the parent compound.

Pharmaceutical Compositions

In another aspect, the present invention provides pharmaceutical compositions, also referred to as pharmaceutical formulations that include a therapeutically effective amount of one or more salts of the invention, and a pharmaceutically acceptable carrier or excipient.

While it is possible for the salts of the invention to be administered alone, it is typically preferable to administer them as pharmaceutical compositions. The pharmaceutical compositions of the invention are formulated with conventional carriers and excipients, which are selected in accord with ordinary practice. The carrier(s) must be "acceptable" in the sense of being compatible with the other ingredients of the formulation and physiologically innocuous to the recipient thereof. Tablets contain such components as excipients, glidants, fillers, binders and the like. Aqueous formulations are prepared in sterile form, and when intended for delivery by other than oral administration they are generally isotonic. All formulations optionally contain excipients such as those set forth in the *Handbook of*

*Pharmaceutical Excipients* (R. C. Rowe et al., Pharmaceutical Press, 5th ed., 2006). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

The formulations may conveniently be presented in unit dosage form (e.g., tablet) and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of salts of the invention contain the active materials in admixture with excipients suitable for the manufacture of aqueous suspensions. Such excipients can include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending, for example, upon the particular mode of administration. For example, a time-release formulation intended for oral administration to humans may contain approximately 1 to 1000 mg of active material compounded with an appropriate and convenient amount of carrier material which may vary from about 5 to about 95% of the total composition (weight:weight).

Formulations suitable for administration to the eye include eye drops wherein the active ingredient is dissolved or suspended in a suitable carrier, especially an aqueous solvent for the active ingredient.

Formulations suitable for topical administration in the mouth include lozenges comprising the active ingredient in a flavored basis, such as sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments of microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of conditions associated with HIV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose or an appropriate fraction thereof, of the active ingredient. Thus, for example, a daily dose of a salt of the present invention can be provided in a single tablet, or in multiple tablets (e.g., two or three tablets).

It should be understood that in addition to the ingredients particularly mentioned above the formulations of this invention may include other agents conventional in the art having regard to the type of formulation in question, for example those suitable for oral administration may include flavoring agents.

Pharmaceutical formulations that are also within the scope of the invention provide controlled release of the active ingredient to allow less frequent dosing or to improve the pharmacokinetic or toxicity profile of the active ingredient. Accordingly, the invention also provides pharmaceutical compositions comprising one or more salts of the invention formulated for sustained or controlled release.

An effective dose of a salt of the present invention depends, for example, on whether the salt is being used prophylactically (typically a lower dose is required compared to therapeutic use of the same salt), the method of delivery, and the pharmaceutical formulation, and will be determined by the clinician using conventional dose escalation studies. An effective dose can be expected to be from about 0.0001 mg/kg body weight per day to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily dose for an adult human of approximately 70 kg body weight will typically range from 1 mg to 1000 mg, preferably between 5 mg and 500 mg, and may take the form of single or multiple doses. By way of example, the dose of a salt of the present invention in a unit dose formulation to be administered once per day may be from 1 mg to 100 mg, such as from 30 mg to 60 mg, such as a 30 mg daily dose or a 60 mg daily dose.

Combination Therapy

Each of the citrate, succinate and malonate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate may be employed in combination with other therapeutic agents for the treatment or prophylaxis of AIDS and/or one or more other diseases present in a human subject suffering from AIDS (e.g., bacterial and/or fungal infections, other viral infections such as hepatitis B or hepatitis C, or cancers such as Kaposi's sarcoma). The additional therapeutic agent(s) may be coformulated with one or more salts of the invention (e.g., coformulated in a tablet).

Examples of such additional therapeutic agents include agents that are effective for the treatment or prophylaxis of viral, parasitic or bacterial infections, or associated conditions, or for treatment of tumors or related conditions, include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-arabinosyl)-5-iodocytidine (FLAC), tetrahydroimidazo(4,5,1-jk)-(1,4)-benzodiazepin-2(1H)-thione (TIBO), 2'-nor-cyclicGMP, 6-methoxypurine arabinoside (ara-M), 6-methoxypurine arabinoside 2'-O-valerate; cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI); acyclic nucleosides such as acyclovir, penciclovir, famciclovir, ganciclovir, HPMPC, PMEA, PMEG, PMPA. PMPDAP, FPMPA, HPMPA, HPMPDAP, (2R,5R)-9-tetrahydro-5-(phphohonomethoxy)-2-furanyladenine, (2R,5R)-1-tetrahydro-5-(phosphonomethoxy)-2-furanylthymine; other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformnate); antibacterial agents including bactericidal fluoroquinolones (ciprofloxacin, pefloxacin and the like); aminoglycoside bactericidal antibiotics (streptomycin, gentamicin, amicacin and the like); β-lactamase inhibitors (cephalosporins, penicillins and the like); other antibacterials including tetracycline, isoniazid, rifampin, cefoperazone, claithromycin and azithromycin, antiparasite or antifungal agents including pentamidine (1,5-bis(4'-aminophenoxy)pentane), 9-deaza-inosine, sulfamethoxazole, sulfadiazine, quinapyramine, quinine, fluconazole, ketoconazole, itraconazole, Amphotericin B, 5-fluorocytosine, clotrimazole, hexadecyiphosphocholine and nystatin; renal excretion inhibitors such as probenicid; nucleoside transport inhibitors such as dipyridamole, dilazep and nitrobenzylthioinosine, immunomodulators such as FK506, cyclosporin A, thymosin α-1; cytokines including TNF and TGF-β; interferons including IFN-α, IFN-β, and IFN-γ; interleukins including various interleukins, macrophage/granulocyte colony stimulating factors including GM-CSF, G-CSF, M-CSF, cytokine antagonists including anti-TNF antibodies, anti-interleukin antibodies, soluble interleukin receptors, protein kinase C inhibitors and the like.

Examples of suitable active therapeutic agents or ingredients which can be combined with the salts of the invention, and which have activity against HIV, include 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG11859, DG35, L-756423, RO0334649, KNI-272, DPC-681, DPC-684, and GW640385X, DG17. PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine. MIV-210, racivir (−FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+ emtricitabine, tenofovir disoproxil fumarate+emtricitabine+ efavirenz, and adefovir, 5) a HIV integrase inhibitor, e.g., curcumin, derivatives of curcumin, chicoric acid, derivatives of chicoric acid, 3,5-dicaffooylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercctin, S-1360, zintevir (AR-177), L-870812, and L-870810. MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050. PF-232798, CCR5mAb004, and maraviroc, 11) an interferon, e.g., pegylated rIFN-alpha 2b, pegylated rIFN-alpha 2a, rIFN-alpha 2b. IFN alpha-2b XL, rIFN-alpha 2a, consensus IFN alpha, infergen, rebif locteron, AVI-005, PEG-infergen, pegylated IFN-beta, oral interferon alpha, feron, reafermn, intermax alpha, r-IFN-beta, infergen+actimmune, IFN-omega with DUROS, and albuferon, 12) ribavirin analogs, e.g., rebetol, copegus, levovirin. VX-497, and viramidine (taribavirin) 13) NS5a inhibitors, e.g., A-831 and A-689, 14) NS5b polymerase inhibitors, e.g., NM-283, valopicitabine, R1626, PSI-6130 (R1656). HIV-796, BILB 1941. MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HIV, e.g., benzimidazole derivatives, benzo-1,2,4-thiadiazine derivatives, and phenylalanine derivatives, 19) other drugs for treating HIV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, 01-5005, ANA-975 (isatoribine), XTL-6865, ANA 971, NOV-205, tarvacin, EHC-18, and NIM811, 19) pharmacokinetic enhancers, e.g., BAS-100 and SPI452, 20) RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

Again by way of example, the following list discloses exemplary HIV antivirals, with their corresponding U.S. Patent numbers that can be combined with the salts of the present invention.

Exemplary HIV Antivirals and Patent Numbers

Ziagen (Abacavir sulfate, U.S. Pat. No. 5,034,394)
Epzicom (Abacavir sulfate/lamivudine, U.S. Pat. No. 5,034, 394)
Hepsera (Adefovir dipivoxil, U.S. Pat. No. 4,724,233)
Agenerase (Amprenavir, U.S. Pat. No. 5,646,180)
Reyataz (Atazanavir sulfate, U.S. Pat. No. 5,849,911)
Rescriptor (Delavirdine mesilate, U.S. Pat. No. 5,563,142)
Hivid (Dideoxycytidine; Zalcitabine, U.S. Pat. No. 5,028, 595)
Videx (Dideoxyinosine; Didanosine, U.S. Pat. No. 4,861, 759)
Sustiva (Efavirenz, U.S. Pat. No. 5,519,021)
Emtriva (Emtricitabine. U.S. Pat. No. 6,642,245)
Lexiva (Fosamprenavir calcium, U.S. Pat. No. 6,436,989)
Virudin; Triaptern Foscavir (Foscarnet sodium, U.S. Pat. No. 6,476,009)
Crixivan (Indinavir sulfate, U.S. Pat. No. 5,413,999)
Epivir (Lamivudine, U.S. Pat. No. 5,047,407)
Combivir (Lamivudine/Zidovudine, U.S. Pat. No. 4,724, 232)
Aluviran (Lopinavir)
Kaletra (Lopinavir/ritonavir, U.S. Pat. No. 5,541,206)
Viracept (Nelfinavir mesilate, U.S. Pat. No. 5,484,926)
Viramune (Nevirapine, U.S. Pat. No. 5,366,972)
Norvir (Ritonavir, U.S. Pat. No. 5,541,206)
Invirase; Fortovase (Saquinavir mesilate, U.S. Pat. No. 5,196,438)
Zerit (Stavudine, U.S. Pat. No. 4,978,655)
Truvada (Tenofovir disoproxil fumarate/emtricitabine, U.S. Pat. No. 5,210,085)
Aptivus (Tipranavir)
Retrovir (Zidovudine; Azidothymidine, U.S. Pat. No. 4,724, 232)

Methods of Inhibition of HIV

In a further aspect, the present invention provides methods of treating Acquired Immune Deficiency Syndrome (AIDS), wherein each method includes the step of administering to a human being suffering from AIDS a therapeutically effective amount of a salt of the invention, or a hydrate of a salt of the invention. Treatment of AIDS includes the amelioration of at least one symptom of AIDS, and/or slowing or preventing the progression of the disease. Typically the therapeutically effective amount of the salt is administered to a human being in the form of a pharmaceutical composition, as described under the heading "Pharmaceutical Compositions". Typically, the pharmaceutical composition is administered orally, for example in the form of a tablet. Examples of therapeutically effective daily doses of one or more salts of the invention, or hydrates thereof are from 1 mg to 100 mg, such as from 10 mg to 30 mg. The salts of the invention can be administered daily, for example in the form of one or more tablets that include an amount of salt that provides an effective amount, such as 10 mg or 30 mg or 60 mg, of the free base when the salt dissociates in an aqueous medium within the human body.

Routes of Administration

One or more salts of the invention are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with, for example, the condition of the recipient. An advantage of the salts of the present invention is that they are orally bioavailable and can be dosed orally.

EXAMPLES AND EXEMPLARY EMBODIMENTS

See also WO 2006/110157, the disclosure of which is herein incorporated by reference in its entirety, particularly, pages 167-174.

Example 1. Synthesis of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate

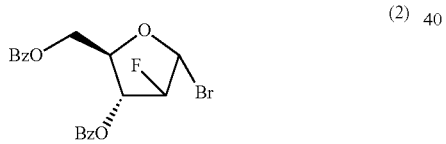

(2)

2-deoxy-2-fluoro-3,5-di-O-benzoyl-a-D-arabinofurauosylbromide (2)

Compound (2) was synthesized according to the synthetic schemes disclosed in Tann et. al., JOC, 1985, Vol. 50 pg. 3644 and Howell et. al., JOC, 1988, Vol. 53, pg. 85.

To a solution of 1,3,5-tri-O-benzoyl-2-deoxy-2-fluoro-α-D-arabinofuranose (1) (120 g, 258 mmol), commercially available from Davos or CMS chemicals, in CH$_2$Cl$_2$ (1 L) was added 33% HBr/Acetic acid (80 mL). The mixture was stirred at room temperature for 16 h, cooled with ice-water, and slowly neutralized over 1-2 h with NaHCO$_3$ (150 g/1 0.5 L solution).

The CH$_2$Cl$_2$ phase was separated and concentrated under reduced pressure. The residue was dissolved in ethyl acetate and washed with NaHCO$_3$ until no acid was present. The organic phase was dried over MgSO$_4$, filtered and concentrated under reduced pressure to give product 2 as a yellow oil (~115 g).

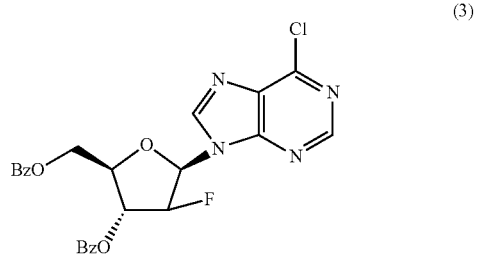

2-deoxy-2-fluoro-3, 5-dl-O-benzoyl-j-D-arabinofuranosyl-9H-6-chloropurine (3)

Compound (3) was synthesized according to the synthetic schemes disclosed in Ma et. al., J. Med. Chem., 1997, Vol. 40, pg. 2750; Marquez et. al., J. Med. Chem., 1990, Vol. 33, pg. 978; Hildebrand et. al., 3. Org. Chem., 1992, Vol. 57, pg. 1808 and Kazimierczuk et. al., JACS, 1984, Vol. 106, pg. 6379.

To a suspension of NaH (14 g, 60%) in Acetonitrile (900 mL), 6-chloropurine (52.6 g) was added in 3 portions. The mixture was stirred at room temperature for 1.5 h. A solution of 2 (258 mmol) in Acetonitrile (300 mL) was added dropwise. The resulting mixture was stirred at room temperature for 16 h. The reaction was quenched with Acetic acid (3.5 mL), filtered and concentrated under reduced pressure. The residue was partitioned between CH$_2$Cl$_2$ and water. The organic phase was dried over MgSO$_4$, filtered and concentrated. The residue was treated with CH$_2$Cl$_2$ and then EtOH (~1:2 overall) to precipitate out the desired product 3 as a yellowish solid (83 g, 65% from 1).

2-deoxy-2-fluoro-β-D-arabinofuranosyl-6-methoxyadenine (4)

To a suspension of 3 (83 g, 167 mmol) in Methanol (1 L) at 0° C., NaOMe (25% wt, 76 mL) was added. The mixture was stirred at room temperature for 2 h, and then quenched with Acetic acid (~11 mL, pH=7). The mixture was concentrated under reduced pressure and the resultant residue partitioned between hexane and water (approximately 500 mL hexane and 300 mL water). The aqueous layer was separated and the organic layer mixed with water once again (approximately 300 mL). The water fractions were combined and concentrated under reduced pressure to ~100 mL. The product, 4, precipitated out and was collected by filtration (42 g, 88%).

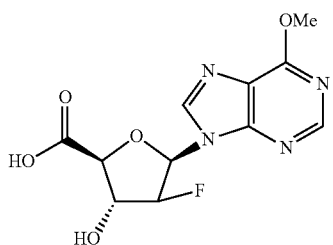

2-deoxy-2-fluoro-5-carboxy-β-D-arabinofuranosyl-6-methoxyadenine (5)

Compound (5) was synthesized according to the synthetic schemes disclosed in Moss et. al., J. Chem. Soc., 1963, pg. 1149.

A mixture of Pt/C (10%, 15 g (20-30% mol equiv.) as a water slurry) and NaHCO$_3$ (1.5 g, 17.94 mmol) in H$_2$O (500 mL) was stirred at 65° C. under H$_2$ for 0.5 h. The reaction mixture was then allowed to cool, placed under a vacuum and flushed with N$_2$ several times to completely remove all H$_2$. Compound 4 (5.1 g, 17.94 mmol) was then added at room temperature. The reaction mixture was stirred at 65° C. under O$_2$ (balloon) until the reaction was complete by LC-MS (typically 24-72 h). The mixture was cooled to room temperature and filtered. The Pt/C was washed with H$_2$O extensively. The combined filtrates were concentrated to ~30 mL, and acidified (pH 4) by the addition of HCl (4N) at 0° C. A black solid precipitated out which was collected by filtration. The crude product was dissolved in a minimum amount of Methanol and filtered through a pad of silica gel (eluting with Methanol). The filtrate was concentrated and crystallized from water to give compound 5 (2.5 g) as an off-white solid.

for 30 min, then cooled to room temperature and concentrated under reduced pressure. The residue was partitioned between ethyl acetate and water. The organic phase was separated and washed with NaHCO$_3$ followed by brine, dried over MgSO$_4$, filtered and concentrated under reduced pressure. The residue and diethyl (hydroxymethyl)phosphonate (33 mL, 225 mmol) were dissolved in CH$_2$Cl$_2$ (250 mL) and cooled down to −40° C. A solution of iodine monobromide (30.5 g, 1.1 mol) in CH$_2$Cl$_2$ (100 mL) was added dropwise. The mixture was stirred at −20 to −5° C. for 6 h. The reaction was then quenched with NaHCO$_3$ and Na$_2$S$_2$O$_3$. The organic phase was separated and the water phase was extracted with CH$_2$Cl$_2$. The combined organic phases were washed with brine, dried over MgSO$_4$, filtered and concentrated under reduced pressure. The residue was purified by silica gel chromatography to give product 6 (6 g, 15.3%).

Alternative Procedure for the Preparation of 6

A solution of 5 (2.0 g, 6.7 mmol) in THF (45 mL) was treated with triphenyl phosphine (2.3 g, 8.7 mmol) under N$_2$. Diisopropyl azodicarboxylate (1.8 g, 8.7 mmol) was added slowly. The resultant mixture was stirred at room temperature for 1 h and then concentrated under reduced pressure to dryness. The residue was dissolved in CH$_2$Cl$_2$ (20 ml), and then treated with diethyl(hydroxymethyl)phosphonate (4.5 g, 27 mmol). The mixture was cooled to −60° C. and then a cold solution of iodine monobromide 2 g, 9.6 mmol) in CH$_2$Cl$_2$ (10 ml) was added. The reaction mixture was warmed to −10° C. and then kept at −10° C. for 1 h. The reaction mixture was diluted with CH$_2$Cl$_2$, washed with saturated aqueous NaHCO$_3$, and then with aqueous sodium thiosulfate. The organic phase was separated, dried over MgSO$_4$, and concentrated under reduced pressure to dryness. The reaction mixture was purified by silica gel chromatography (eluting with 25% ethyl acetate in CH$_2$Cl$_2$, then switching to 3% methanol in CH$_2$Cl$_2$) to afford product 6 (0.9 g, 33%).

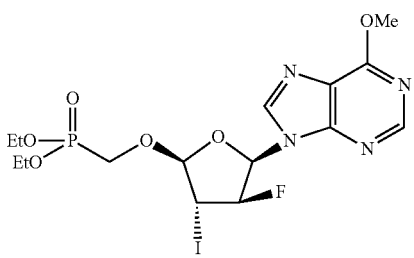

(2'R, 3'S, 4'R, 5'R)-6-Methoxy-9-[tetrahydro 4-iodo-3-fluoro-5-(diethoxyphosphinyl)methoxy-2-furanyl]purine (6)

Compound (6) was synthesized according to the synthetic schemes disclosed in Zemlicka et. al., 1. Amer. Chem., Soc., 1972, Vol. 94, pg. 3213.

To a solution of 5 (22 g, 73.77 mmol) in DMF (400 mL), DMF dineopentyl acetal (150 mL, 538 mmol) and methanesulfonic acid (9.5 mL, 146.6 mmol) were added. The reaction mixture was stirred at 80-93° C. (internal temperature)

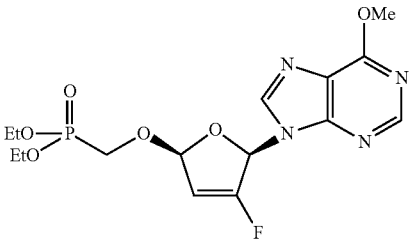

(2'R, 5'R)-6-Methoxy-9-[3-fluoro-2,5-dihydro-5-(diethoxyphosphinyl)methoxy-2-furanyl]purine (7)

To a solution of compound 6 (6 g, 11.3 mmol) in acetic acid (2.5 mL) and methanol (50 mL), NaClO (10-13%) (50 mL) was added dropwise. The reaction mixture was then stirred for 0.5 h and concentrated under reduced pressure. The residue was treated with ethyl acetate and then filtered to remove solids. The filtrate was concentrated and the residue was purified by silica gel chromatography to give product 7 (4 g, 88%).

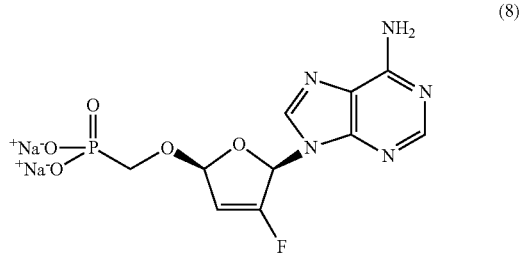

(2'R,5'R)-9-(3-fluoro-2,5-dihydro-5-phosphonomethoxy-2-furanyl)adenine disodium salt (8)

A solution of compound 7 (2.3 g, 5.7 mmol) in methanol (6 mL) was mixed with ammonium hydroxide (28-30%) (60 mL). The resultant mixture was stirred at 120° C. for 4 h, cooled, and then concentrated under reduced pressure. The residue was dried under vacuum for 12 h. The residue was dissolved in DMF (40 mL) and bromotrimethylsilane (3.5 mL) was added. The mixture was stirred at room temperature for 16 h, and then concentrated under reduced pressure. The residue was dissolved in aqueous NaHCO$_3$ (2.3 g in 100 mL of water). The solution was evaporated and the residue was purified on C-18 (40 μm) column, eluting with water. The aqueous fractions were freeze dried to give di-sodium salt 8 (1.22 g, 57%).

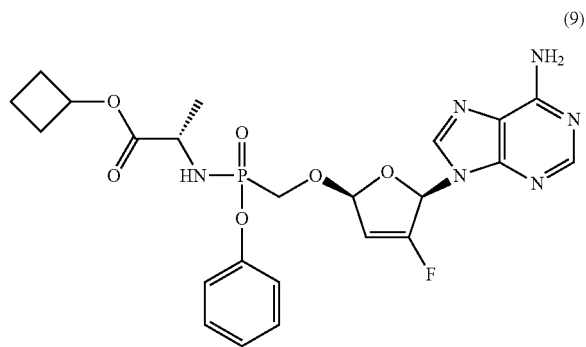 [SMILES: C[C@H](NP(=O)(CO[C@@H]1C=C(F)[C@H](n2cnc3c(N)ncnc32)O1)Oc1ccccc1)C(=O)OC1CCC1]

Example of Monoamidate Preparation (9)

Di sodium salt 8 (25 mg, 0.066 mmol), (S)-Ala-O-cyclobutyl ester hydrochloride (24 mg, 2 eq., 0.133 mmol) and phenol (31 mg, 0.333 mmol) were mixed in anhydrous pyridine (1 mL). Triethylamine (111 μL, 0.799 mmol) was added and the resultant mixture was stirred at 60° C. under nitrogen. In a separate flask, 2'-Aldrithiol (122 mg, 0.466 mmol) and triphenylphosphine (103 mg, 0.466 mmol) were dissolved in anhydrous pyridine (0.5 mL) and the resulting yellow solution was stirred for 15-20 min. The solution was then added to the solution of 8 in one portion. The combined mixture was stirred at 60° C. under nitrogen for 16 h to give a clear yellow to light brown solution. The mixture was then concentrated under reduced pressure. The resultant oil was dissolved in CH$_2$Cl$_2$ and purified by silica gel chromatography (eluting with a linear gradient of 0 to 5% MeOH in CH$_2$Cl$_2$) to give an oil. The resulting oil was dissolved in acetonitrile and water and purified by preparative HPLC (linear gradient, 5-95% acetonitrile in water). Pure fractions were combined and freeze-dried to give mono amidate 9 as a white powder.

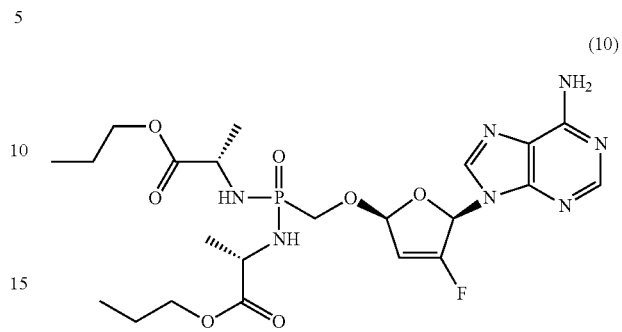

Example of Bis Amidate Preparation (10)

Di sodium salt 8 (12 mg, 0.032 mmol) and (S)-Ala-O-n-Pr ester hydrochloride (32 mg, 6 eq., 0.192 mmol) were mixed in anhydrous pyridine (1 mL). Triethylamine (53 μL, 0.384 mmol) was added and the resultant mixture was stirred at 60° C. under nitrogen. In a separate flask, 2'-Aldrithiol (59 mg, 0.224 mmol) and triphenylphosphine (49 mg, 0.224 mmol) were dissolved in anhydrous pyridine (0.5 mL) and the resulting yellow solution was stirred for 15-20 min. The solution was then added to the solution of 8 in one portion. The combined mixture was stirred at 60° C. under nitrogen for 16 h to give a clear yellow to light brown solution. The mixture was then concentrated under reduced pressure. The resultant oil was dissolved in CH$_2$Cl$_2$ and purified by silica gel chromatography (eluting with a linear gradient of 0 to 5% MeOH in CH$_2$Cl$_2$) to give an oil. The resulting oil was dissolved in acetonitrile and water and purified by preparative HPLC (linear gradient, 5-95% acetonitrile in water). Pure fractions were combined and freeze-dried to give bis amidate as a white powder.

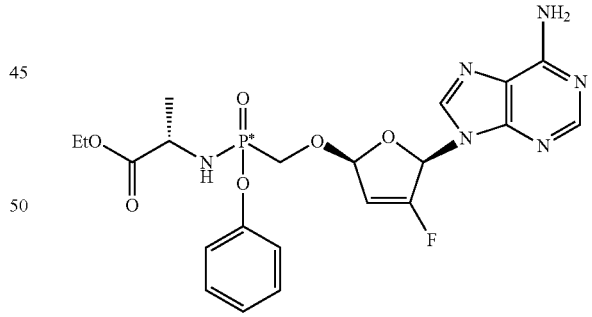

Example of Monoamidate Preparation (11)

Compound 8 (1.5 g, 4 mmol) was mixed with ethyl alanine ester HCl salt (1.23 g, 8 mmol) and phenol (1.88 g, 20 mmol). Anhydrous pyridine (35 mL) was added followed by TEA (6.7 mL, 48 mmol). The mixture was stirred at 60° C. under nitrogen for 15-20 min. 2'-Aldrithiol (7.3 g) was mixed in a separate flask with triphenylphosphine (6.2 g) in anhydrous pyridine (5 mL) and the resultant mixture was stirred for 10-15 min to give a clear light yellow solution. The solution was then added to the above mixture and stirred overnight at 60° C. The mixture was concentrated under reduced pressure to remove pyridine. The resultant residue was dissolved in ethyl acetate and washed with saturated sodium bicarbonate solution (2×) and then with saturated sodium chloride solution. The organic layer was dried over sodium sulfate, filtered and then concentrated under reduced pressure. The resultant oil was dissolved in dichloromethane and loaded onto a dry CombiFlash column, 40 g, eluting with a linear gradient of 0-5% methanol in dichloromethane over 10 min and then 5% methanol in dichloromethane for 7-10 min. Fractions containing the desired product were combined and concentrated under reduced pressure to give a foam. The foam was dissolved in acetonitrile and purified by prep HPLC to give 11 (0.95 g).

Dissolved 11 (950 mg) in small amount of acetonitrile and let stand at room temperature overnight. Collected solid by filtration and washed with small amount of acetonitrile. Filtrate was reduced under vacuum and then loaded onto Chiralpak AS-H column equilibrated in Buffer A, 2% ethanol in acetonitrile. Isomer A, 12, was eluted out with Buffer A at 10 mL/min for 17 mins. After which Buffer B, 50% methanol in acetonitrile, was used to elute isomer B, 13, separately out from the column in 8 mins. Removed all solvent and then separately re-dissolved in acetonitrile and water. Separately freeze-dried the samples (Mass—348 mg). Isomer 12 is shown below

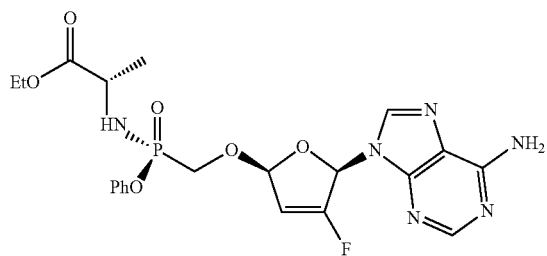

(12)

Example 2. Screening Salt Forms of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate The following acids were screened to determine whether they formed suitable crystalline salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate: Mineral acids (HX, wherein X=halogen; $H_3PO_4$); organic sulfonic acids ($RSO_3H$, wherein R=Me, Et, Ph, (+)-camphor-10-sulfonic acid; naphthalene-2-sulfonic acid; naphthalene-1,5-disulfonic acid); mono carboxylic acids ($RCO_2H$, wherein R=H, Me, Et, Ph, trans-PhCH=CH, $Cl_2CH$, $PhCONHCH_2$), and dicarboxylic acids (malonic, succinic, fumaric, adipic, oxalic, maleic).

Solids were obtained with three of the foregoing acids when mixed with Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate: trifluoroacetic acid, malonic acid, and succinic acid. Trifluoroacetic acid is not considered to be pharmaceutically acceptable.

Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is an amidate prodrug which undergoes decomposition in protic solvents under acidic or basic conditions. For this reason, acids with potentially nucleophilic moieties were not included in the initial round of screening. Subsequently, citric acid, glycolic acid, (S)-(+)-lactic acid, salicylic acid, (S)-(−)-malic acid, (S)-(+)-mandelic acid and (S)-(+)-glutamic acid were evaluated. Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate unexpectedly formed a stable crystalline salt with citric acid. This was an unexpected result because citric acid includes a hydroxyl group which can act as a nucleophile toward the amidate moiety of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate and potentially undergo a reaction therewith in which a covalent bond is formed between Ethyl N—[(S)(({[(2R,5R)-5-(6-amino-9H-purin-9-yl)-4-fluoro-2,5-dihydrofuran-2-yl]oxy}methyl)phenoxyphosphinoyl]-L-alaninate and the hydroxyl group of citric acid with the expulsion of either phenol or alanine ethyl ester.

Example 3. Synthesis of Malonate Salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate The free base form of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate was dissolved in warm 2-butanone (15 parts), and malonic acid (0.26 parts) was added to form a solution with agitation. Heptane (5 parts) was added to the solution which was slowly cooled to about 5° C., collected and rinsed with cold 2-butanone/heptane. The resulting malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate was thereby produced with a yield of about 80%.

The NMR spectrum of the malonate salt had the following characteristics: $^1$H NMR (400 MHz, CHLOROFORM-d) ppm=8.27 (s, 1H), 8.26 (s, 1H), 7.32-7.20 (m, 3H), 7.15 (d, J=7.8 Hz, 2H), 6.78 (m, 1H), 5.88 (br. s., 1H), 5.78 (s, 1H), 4.17 (m, 2H), 4.15-4.07 (m, 3H), 3.85 (dd, J=8.0, 8.0, 1 H), 3.38 (s, 2H), 1.31 (d, J=7.0 Hz, 3H), 1.23 (t, J=7.0 Hz, 3H)
$^{31}$P NMR (162 MHz, CHLOROFORM-d) ppm=20.64 (s)
$^{19}$F NMR (376 MHz, ACETONITRILE-d3) ppm=−135.19 (s)

Example 4. Synthesis of Succinate Salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate The free base form of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate was dissolved in warm 2-butanone (15 parts), and succinic acid (0.28 parts) was added to form a solution with agitation. The solution was slowly cooled to about 5° C., collected, and rinsed with cold 2-butanone, thereby yielding the succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate at a yield of 80%.

The NMR spectrum of the succinate salt had the following characteristics: $^1$H NMR (400 MHz, ACETONITRILE-d3) ppm=8.26 (s, 1H), 8.15 (s, 1H), 7.29 (dd, J=7.6, 7.6 Hz, 2H), 7.16 (d, J=7.6 Hz, 1H), 7.12 (d, J=8.0 Hz, 2H), 6.78 (m, 1H), 6.17 (br s, 1H), 5.89 (m, 2H), 4.12-3.95 (overlapped multiplets, 6H), 2.53 (s, 4H), 1.24 (d, J=6.8, 3 H), 1.18 (t, J=7.2, 3 H).

$^{31}$P NMR (162 MHz, Acetonitrile-d3) ppm=21.60 (s)
$^{19}$F NMR (376 MHz, Acetonitrile-d3) ppm=−135.19 (s)

Example 5. Synthesis of Citrate Salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate The free base form of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate (about 30 g) was dissolved in hot acetonitrile (16 parts) and citric acid (0.38 parts) were added with agitation. The resulting solution was slowly cooled to about 5° C. collected and rinsed with cold acetonitrile, and dried, thereby affording the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate with a yield of about 84%.

The NMR spectrum of the citrate salt had the following characteristics: $^1$H NMR (400 MHz, DMSO-d6) ppm=8.20 (s, 2H), 7.45 (2H, br s), 7.29 (dd, J=7.6, 7.6 Hz, 2H), 7.13 (dd, J=7.2 Hz, J=7.2 Hz 1H), 7.12 (dd, J=8.0 Hz, J=8.0 Hz 2H), 6.86 (d, J=2.4 Hz, 1H), 6.14 (s, 1H), 5.97 (d, J=3.6 Hz, 1H), 5.78 (dd, J=12.2, 10.4 Hz, 1H), 4.05 (m, 1H), 4.02 (m, 2H), 3.98 (m, 1H), 3.89 (m, 1H), 2.76 (d, J=15.6 Hz, 2H), 2.66 (d, J=15.6 Hz, 2H), 1.16 (d, J=7.2 Hz, 1H).

$^{31}$P NMR (162 MHz, DMSO-d6) ppm=22.29 (s)
$^{19}$F NMR (376 MHz, ACETONITRILE-d3) ppm=−133.88 (s)

HRMS: m/z: 507.1561; Calcd for $C_{21}H_{24}FN_6O_6P$: 507.1557.

Anal. Calcd for $C_{21}H_{24}FN_6O_6P$: C, 46.42; H, 4.62; N, 12.03; P, 4.43; F, 2.72. Found: C, 45.83; H, 4.74; N, 11.81; P, 4.45; F, 2.80.

Example 6. Physicochemical Properties of Salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate Representative batches of the malonate, succinate, and citrate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate were prepared. The melting points of these salts were determined and serve as a rough measure of stability with a higher melting point indicating a higher level of stability. As shown in Table 1, the citrate salt had the highest melting point. Additionally, the heat of fusion ($\Delta H_{(fusion)}$) of each of the three salts is shown in Table 1. The citrate salt had the highest heat of fusion indicating a higher degree of solid-state crystallinity than the other two salts.

TABLE 1

Melting Temperatures and Heat of Fusion of Succinate, Malonate and Citrate Salts of Ethyl N-[(S)({[(2R,5R)-5-(6-amino-9H-purin-9-yl)-4-fluoro-2,5-dihydrofuran-2-yl]oxy}methyl)phenoxyphosphinoyl]-L-alaninate

| Salt | Molecular Weight | $\Delta H_{(fusion)}$ J/g | $T_m$ (° C.) |
|---|---|---|---|
| Succinate Salt | 624.52 | 58.85 | 138.06 |
| Malonate Salt | 610.49 | 66.10 | 120.13 |
| Citrate Salt | 698.56 | 127.59 | 149.76 |

The free base form of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is amorphous, hygroscopic and chemically unstable when stored under open condition at 40° C. and 75% relative humidity (RH). As shown in Table 2, the corresponding succinate, malonate and citrate salts were not hygroscopic at room temperature when exposed to a relative humidity of 92% for several days.

TABLE 2

Solid State Hygroscopicity of Salt Forms of Ethyl N-[(S)({[(2R,5R)-5-(6-amino-9H-purin-9-yl)-4-fluoro-2,5-dihydrofuran-2-yl]oxy}methyl)phenoxyphosphinoyl]-L-alaninate at Room Temperature

| Salt | Time (days) | 20-25° C./92% RH |
|---|---|---|
| Succinate Salt | 0 | 0.01 |
| | 13 | 0.010 |
| Malonate Salt | 0 | 0.02 |
| | 13 | 0.12 |
| Citrate Salt | 0 | 0.01 |
| | 25 | 0.02 |

The solid-state chemical stability of the free base, succinate, malonate and citrate salts of Ethyl N—[(S)({[(2R,5R)-5-(6-amino-9H-purin-9-yl)-4-fluoro-2,5-dihydrofran-2-yl]oxy}methyl)phenoxyphosphinoyl]-L-alaninate were examined under open conditions at 40° C. and 75% relative humidity. As shown in Table 3, the citrate salt displayed superior chemical stability compared to the succinate and malonate salts.

TABLE 3

Solid State Stability of Free Base form of Ethyl N-{(S)({[(2R,5R)-5-(6-amino-9H-purin-9-yl)-4-fluoro-2,5-dihydrofuran-2-yl]oxy}methyl)phenoxyphosphinoyl]-L-alaninate, and the corresponding Succinate, Citrate and Malonate Salts at 40° C./75% Relative Humidity Under Open Conditions

| Form | Time (days) | Free Base (%) | Other Impurities (%) |
|---|---|---|---|
| Free Base | 0 | 99.01 | 0.99 |
| | 7 | 82.95 | 17.05 |
| | 14 | 66.89 | 33.11 |
| | 22 | 55.90 | 44.10 |
| Succinate Salt | 0 | 98.95 | 1.05 |
| | 9 | 95.15 | 4.85 |
| | 16 | 92.47 | 7.53 |
| | 22 | 90.43 | 9.57 |
| | 30 | 85.92 | 14.08 |
| Malonate Salt | 0 | 97.82 | 2.18 |
| | 9 | 94.66 | 5.34 |
| | 16 | 92.97 | 7.03 |
| | 22 | 93.48 | 6.52 |
| | 30 | 85.84 | 14.16 |
| Citrate Salt | 0 | 98.00 | 2.00 |
| | 4 | 97.27 | 2.73 |
| | 12 | 97.20 | 2.80 |
| | 17 | 95.86 | 4.14 |
| | 27 | 94.59 | 5.41 |

Example 7. Composition of Tablets Providing Equivalent of 10 mg and 30 mg of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate Free Base The citrate salt of Ethyl N—[(S)({[(2R,5R)-5-(6-amino-9H-purin-9-yl)-4-fluoro-2,5-dihydrofuran-2-yl]oxy}methyl)

phenoxyphosphinoyl]-L-alaninate was formulated into 10 mg and 30 mg tablets using the roller compaction process. The active ingredient, lactose anhydrous, microcrystalline cellulose and croscarmellose sodium were first blended, the mixture was then lubricated with one third of the total amount of magnesium stearate, then roller compacted, followed by milling. The resulting granules were lubricated with the remaining amount of magnesium stearate and pressed into tablets.

Table 4 shows the composition of tablets that include the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate, and that provide either 10 mg or 30 mg of the free base form of the compound when the citrate salt dissociates in an aqueous Human transformed CCRF-CEM T-cells were obtained from The American Type Culture Collection (Manassas, Va.) and cultured in RPMI-1640 medium supplemented with 10% FBS and antibiotics. An aliquot of cells ($2-3\times10^6$ cells) was collected at each time point, counted, pelleted by centrifugation, resuspended in 0.5 mL of the original treatment media and layered onto 0.5 mL of Nyosil M25 oil. The samples were spun in a microcentrifuge for 20 seconds at the maximum speed (approximately 800×g). The top layer of media was removed and the oil layer was washed twice with 0.8 mL phosphate-buffered saline. Washing buffer and the oil layer were carefully removed, the cell pellet was resuspended in 0.5 mL 70% methanol and incubated overnight at −70° C. to facilitate cell lysis. Cell lysates were centrifuged, supernatants collected, dried by vacuum and resuspended in

TABLE 4

| Components | % w/w | Tablet Unit Formula (mg/unit) 10 mg | 30 mg | Compendial Reference | Function |
|---|---|---|---|---|---|
| Citrate Salt | 13.79[a] | 13.79[a,b] | 41.37[a,c] | HSE | Active Ingredient |
| Lactose Anhydrous[d] | 66.00 | 66.00 | 198.00 | NF | Diluent/Filler |
| Microcrystalline Cellulose | 15.21 | 15.21 | 45.63 | NF | Binder/Filler |
| Croscarmellose Sodium | 3.50 | 3.50 | 10.50 | NF | Disintegrant |
| Magnesium Stearate | 1.50 | 1.50 | 4.50 | NF | Lubricant |
| Total | 100.00 | 100.00 | 300.00 | | |

[a]Equivalent to 10% 2/2 of free base form of compound. Actual drug substance weight will be adjusted to account for drug substance purity.
[b]Equivalent to 10 mg of free base form of compound.
[c]Equivalent to 30 mg of free base form of compound.
[d]The adjusted drug substance quantity will be subtracted from the quantity of anhydrous lactose.
[e]The abbreviation NF means national formulary, and the abbreviation HSE means House Compendial Reference which is the internal standard used at Gilead Sciences.

Example 8. Comparison of Lymphocyte Loading of Active Metabolite After Administration to Lymphocytes of Ethyl N—[(S)({[(2R5R)-5-(6-amino-9H-purin-9-yl)-4-fluoro-2,5-dihydrofuran-2-yl]oxy}methyl)phenoxyphosphinoyl]-L-alaninate (Prodrug) or Parent Compound Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a prodrug that is hydrolyzed in the human body to yield a hydrolysis product that is hereinafter referred to as "the parent compound". The parent compound is phosphorylated within the human body to produce a biologically active phosphorylated product (hereinafter "the active metabolite") which inhibits the activity of reverse transcriptase enzyme.

To characterize the intracellular metabolism of the prodrug and parent compound, lymphocyte cells were treated with either 1 μM prodrug or 100 μM parent compound for 2, 6, and 24 hours. Peripheral blood mononuclear cells (PBMCs) were isolated from human buffy coats (Stanford Blood Bank, Palo Alto, Calif.) using centrifugation in Ficoll Paque Plus (GE Healthcare, Piscataway, N.J.) according to manufacturer's procedure. PBMCs isolated from 3 to 4 independent donors were maintained in RPMI-1640 media with 20% fetal bovine serum and antibiotics (quiescent state) or were activated in the presence of interleukin 2 (20 units/mL, Roche Biochemicals, Indianapolis, Ind.) and phytohemagglutinin PHA-P (1 μg/mL, Sigma) for 3 to 4 days before the initiation of experiments.

10 μL tetrabutyl ammonium acetate containing the diphosphate of [5-(6-Amino-purin-9-yl)-2,5-dihydro-furan-2-yloxymethyl]-phosphonic acid (the non-fluorinated analog of the active metabolite) as an internal standard.

Transient ion-pairing high-performance liquid chromatography coupled to positive ion electrospray tandem mass spectrometery (LC/MS/MS) was used to quantitate intracellular nucleotides. Methods were adapted from those described for the acyclic phosphonate nucleotide analog adefovir, its phosphorylated metabolites and natural nucleotides (Vela, J. E. et al. Simultaneous quantitation of the nucleotide analog adefovir, its phosphorylated anabolites and 2'-deoxyadenosine triphosphate by ion-pairing LC/MS/MS. Journal of Chromatography B Anal. Technol. Biomed. Life Sci., vol. 848, 2007, pp 335-343). Standard curves and quality control samples were generated for all analytes using extracts from untreated cells. Seven point standard curves generally ranged from 0.03 to 20 pmol/million cells and had linearity in excess of $r^2$ equal to 0.99 for all analytes. The lower limits of quantitations for all analytes ranged from 0.05 to 0.1 pmol/million cells. Low and high concentration quality control samples (typically 0.2 and 10 pmol/million cells, respectively) were run with each analyte at the beginning and end of each analytical run to assure accuracy and precision within 20%.

The parent compound was incubated at a 100-fold higher concentration (100 μM) than the prodrug (1 μM) to facilitate accurate analysis of the much lower intracellular accumulation of metabolites observed following incubation of lymphocytes with the parent compound. As shown in Table 5, the prodrug induced 76-, 290- and 140-fold increased levels of the active metabolite relative to the parent compound following incubation with CEM-CCRF, quiescent PBMCs and activated PBMCs, respectively. Active metabolite levels were normalized based on extracellular concentration following incubations with 1 μM prodrug or with 100 μM parent compound.

TABLE 5

| | Dose Normalized Active Metabolite Concentration ((pmol/million)/1 μM media concentration) | | |
|---|---|---|---|
| | CEM-CCRF | Quiscent PBMC | Activated PBMC |
| Parent Compound | 0.087 ± 0.014 | 0.012 ± 0.004 | 0.045 ± 0.004 |
| Prodrug | 6.57 ± 1.00 | 3.52 ± 0.96 | 6.45 ± 1.64 |

Values represent the mean ± standard deviation of three independent experiments performed in duplicate

Example 9. Comparison of Anti-HIV Activity of the Prodrug and the Parent Compound The terms "prodrug" and "parent compound" have the meanings set forth in Example 8.

MT-2 cells were maintained in RPMI-1640 medium supplemented with antibiotics and 10% fetal bovine serum (FBS). MT-2 cells were infected with HIV-1 IIIB at a multiplicity of infection (moi) of 0.01 and added to 96-well plates with serial dilutions of tested compounds at a density of 20,000 cells/well. After a 5-day incubation, the virus-induced cytopathic effect was determined using a CellTiter-Glo™ cell viability assay (Promega. Madison, Wis.) and expressed as a percentage of the signal from samples with fully suppressed virus replication after the subtraction of signal from the untreated control. The concentration of each drug that inhibited the virus-induced cytopathic effect by 50% ($EC_{50}$) was determined by non-linear regression. Activity against NRTI-resistant mutants was determined in parallel with wild-type control virus and fold change in $EC_{50}$ was calculated.

Human peripheral blood mononuclear cells (PBMC) were isolated from donor buffy coats using centrifugation in Ficoll Paque Plus and activated for 4-5 days in RPMI-1640 medium with 20% FBS, antibiotics, interleukin-2 (20 units/mL) and phytohemagglutinine PHA-P (1 μg/mL). Activated PBMC were infected with HIV-1 BaL for 3 hours, washed, seeded into 96-well plates (250,000 cells/well) and incubated with serial dilutions of tested compounds for 5 days, at which point cell supernatants were collected and virus production was determined using commercial HIV-1 p24 ELISA (Beckman Coulter, Miami, Fla.). The concentration of each drug inhibiting the p24 antigen production by 50% (EC50) was determined by regression analysis.

The effect of the addition of pro-moieties on the anti-HIV activity was assessed in MT-2 and stimulated PBMC infected with HIV-1. As shown in Table 6, the prodrug was 71- and 2,300-fold more potent than the parent compound in MT-2 and activated PBMC, respectively.

TABLE 6

Anti-HIV-1 activity of the prodrug and the parent compound in a lymphoid derived cell line and primary lymphoid cells.

| | $EC_{50}$ (μM) | |
|---|---|---|
| | MT-2 | PBMC |
| Parent Compound | 10.6 ± 2.4 | 8.5 ± 7.7 |
| Prodrug | 0.15 ± 0.04 | 0.0037 ± 0.0001 |

Values represent the mean ± standard deviation from at least two dependent experiments performed in triplicate.

Example 10. Oral Bioavailability of the Citrate Salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate After Administration in Tablet Form to Beagle Dogs The dosing group consisted of 3 non-naïve male beagle dogs. The animals were fasted overnight prior to dose administration and up to 4 hr after dosing. Dogs were administered a single tablet containing 41.38 mg of the citrate salt of the prodrug (providing 30 mg of the prodrug per tablet). The tablet consisted of 13.79% of the citrate salt of the prodrug, 66% anhydrous lactose, 15.21% microcrystalline cellulose, 3.5% sodium croscamellose and 1.5% magnesium stearate on a weight per weight basis. Plasma samples were obtained prior to dosing (0 hr) and at 0.083, 0.25, 0.50, 1.0, 2.0, 4.0, 8.0, 12, 24 hr. The blood samples were collected into Vacutainer™ tubes containing EDTA-$K_3$. The blood samples were centrifuged at 4° C. to separate plasma. An aliquot of 100 μl of each plasma sample was first diluted with 300 μl 80% acetonitrile/water containing 200 nM internal standard. Following centrifugation of the protein precipitate, 100 μl of the supernatant was removed and used for analysis. Standard curves and quality control samples were prepared in dog plasma from animals not dosed with the prodrug. Samples were analyzed by a partially validated liquid chromatography couple to triple quadrupole mass spectrometry method.

Administration of the citrate salt of the prodrug as a tablet resulted in rapid absorption of the prodrug and the parent compound derived from the prodrug. As summarized in Table 7, plasma exposure to the prodrug and the parent compound was observed following administration. The oral bioavailability of intact prodrug was 11.4%. These results were not markedly different from those observed following oral administration of the prodrug in a solution formulation, illustrating the effectiveness of the tablets containing the citrate salt of the prodrug to deliver the prodrug and its metabolites into the systemic circulation.

TABLE 7

Mean Plasma Pharmacokinetic Parameters for the Prodrug and the Parent Compound Following Oral Administration of a Tablet Formulation of the Citrate Salt of the Prodrug at a mean dose of 3.05 mg/kg equivalents (Mean, n = 3)

| | Value | |
|---|---|---|
| Parameter | Prodrug | Parent Compound |
| $T_{max}$ (hr) | 0.58 | 2.33 |
| $C_{max}$ (nM) | 1,560 | 959 |
| $AUC_{0-t}$ (nM · hr) | 587 | 7,600 |
| $AUC_{0-8}$ (nM · hr) | 608 | 9,630 |

TABLE 7-continued

Mean Plasma Pharmacokinetic Parameters for the Prodrug and the Parent Compound Following Oral Administration of a Tablet Formulation of the Citrate Salt of the Prodrug at a mean dose of 3.05 mg/kg equivalents (Mean, n = 3)

| Parameter | Value | |
|---|---|---|
| | Prodrug | Parent Compound |
| $t_{1/2}$ (hr) | 0.289 | 11.7 |
| % F[a] | 11.4 | Not Determined |

[a]Calculated based on a mean plasma $AUC_{0-t}$ of 818 nM · hr observed following a 30 minute intravenous Infusion of 0.5 mg/kg GS-9131 to beagle dogs.

Example 11. Differential Scanning Calorimetry (DSC) of Citrate, Malonate and Succinate Salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate Differential scanning calorimetry accurately measures temperatures and heat flow associated with thermal transitions in a material. The DSC traces of the inventive salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate were generated using a TA Instrument (New Castle, Del.) DSC 2010 at a scan rate of 5° C. min$^{-1}$. FIG. 1 shows the characteristic DSC trace for the malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate. The DSC thermogram revealed a single endotherm corresponding to the melting point (120.43° C., $\Delta H_f$=73.72 J/g) followed by a single exotherm corresponding to the decomposition of the malonate salt.

Figure 2:
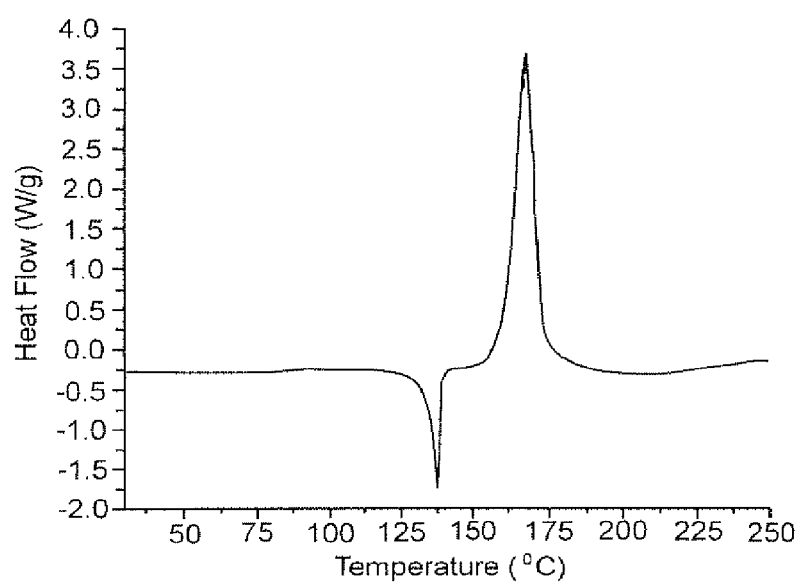
FIG. 2 shows a characteristic DSC trace for the succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

FIG. 2 shows the characteristic DSC trace for the succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate. The DSC thermogram of the succinate salt of GS-9131 revealed a single emdotherm corresponding to the melting point (137.44° C., $\Delta H_f$=66.18 J/g) followed by a single exotherm corresponding to the decomposition of the salt.

Figure 3:
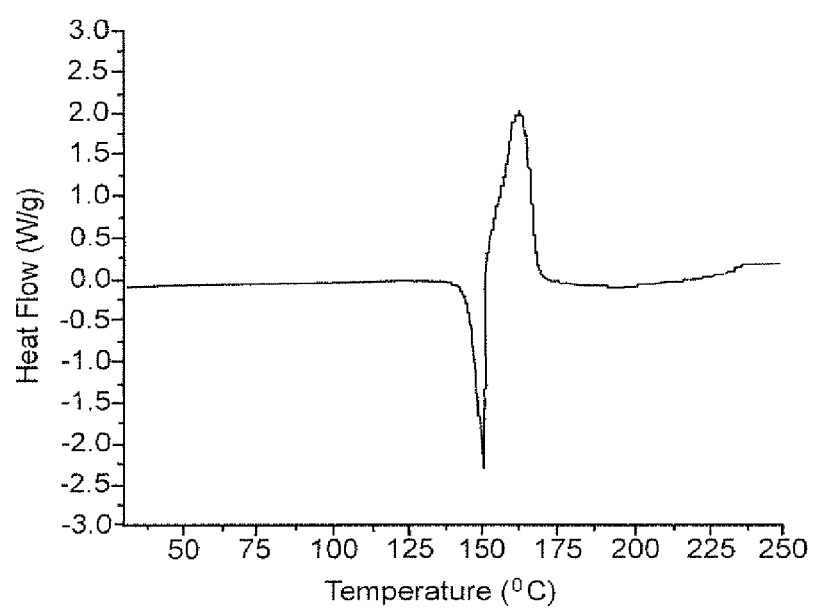
FIG. 3 shows a characteristic DSC trace for the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

FIG. 3 shows the characteristic DSC trace for the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate. The DSC thermogram of the citrate salt revealed a single endotherm corresponding to the melting point (149.41° C., $\Delta H_f$=85.72 J/g) followed by a single exotherm corresponding to the decomposition of the citrate salt.

The citrate salt has a significantly greater heat of fusion than the malonate and succinate salts, indicating a higher degree of solid-state crystallinity.

Example 12. X-Ray Diffraction (XRD) Analysis of the Citrate, Malonate and Succinate Salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate The X-ray powder diffraction (XRPD) patterns of the inventive salts of Ethyl N—[(S)({[(2R,5R)-5-(6-amino-9H-purin-9-yl)-4-fluoro-2,5-dihydrofuran-2-yl]oxy}methyl) phenoxyphosphinoyl]-L-alaninate were generated using two methods. In the first method, a Shimadzu XRD 6000 instrument with the following attributes was used: Cu X-ray tube, 2.2 KW, NF (normal focus); monochromator curved graphite; goniometer vertical, 185 mm radius; divergence slits: 0.5°, 1.0°, 0.05 mm; soller slits: 0.05, 1°, 2°; receiving slits: 0.15 mm, 0.3 mm; scintillation detector (NaI) HV 500-1200.

In the second method, a Shimadzu XRD 6000 instrument with the following attributes was used: Cu target X-ray tube, 35 kv, current 40 ma; continuous scan, monochromator, divergence slit, 1°; soller slit 1°, receiving slit 0.3 mm.

XRPD data for the malonate and succinate salts were obtained using method 1. XRPD data for the citrate salt was obtained using method 2.

It is understood that experimental deviations can slightly change the XRPD absorption band (peak) information. Thus, the numbers reported in this patent resulting from XRPD patterns of the inventive salts will be the same or essentially the same as the numbers which will occur upon repeating the tests. "Essentially the same" in this context means that typical peak position and intensity variability are taken into account (as they normally would be for any analytical technique). For example, one skilled in the art will appreciate that the peak positions will show some inter-apparatus variability. For example, the 2-theta peak positions typically deviate by as much as 0.1 degrees. Further, one skilled in the art will appreciate that relative peak intensities will also show variability due to the degree of crystallinity, preferred orientation, prepared sample surface, and other factors known in the art. Thus, the relative peak intensities should be taken as qualitative measure only.

Figure 4:
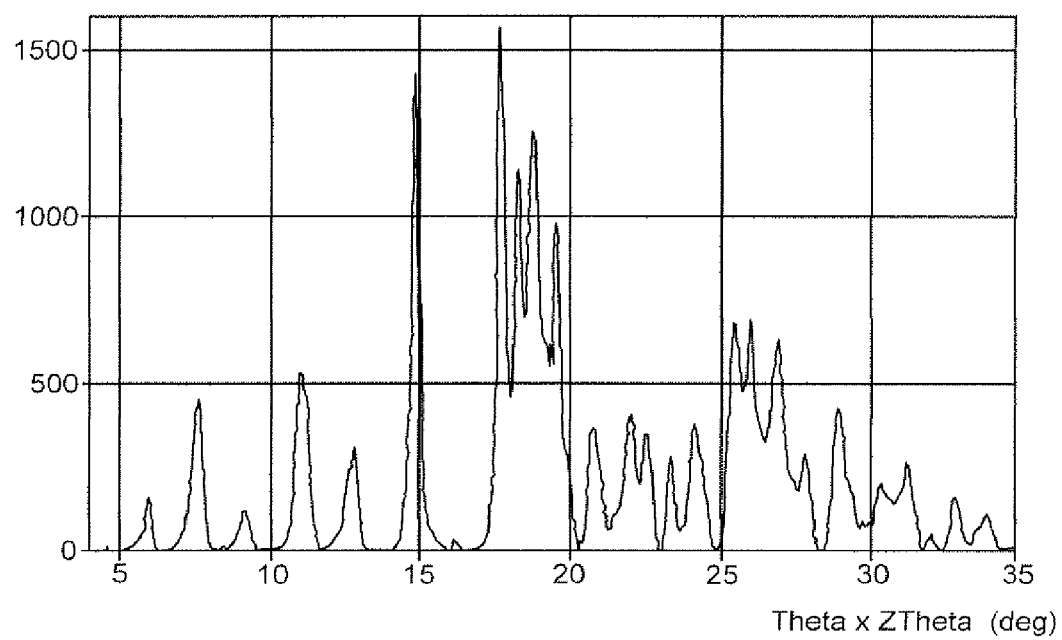
FIG. 4 shows a characteristic X-ray powder diffraction (XRPD) pattern for the malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

FIG. 4 shows the characteristic XRPD pattern for the malonate salt. The principal and characteristic peaks that define this crystalline form of the malonate salt are shown in Tables 8A and 8B.

TABLE 8A

Malonate Salt PXRD Peaks

| Strongest Peaks | 2Theta (deg) | d (A) | FWHM (deg) | Integrated Int |
|---|---|---|---|---|
| 1 | 17.76 | 4.9912 | 0.3190 | 16049 |
| 2 | 14.92 | 5.9342 | 0.3023 | 14513 |
| 3 | 18.80 | 4.7163 | 0.6572 | 21597 |

TABLE 8B

* Basic Data Process *

| Group Name | |
|---|---|
| Data Name | 34984B |
| File Name | 34984B.PKR |
| Sample Name | Lot# 2587-168-17 |
| Comment | Salts USP <941> |

Strongest 3 peaks

| no. | peak no. | 2Theta (deg) | d (A) | I/I1 | FWHM (deg) | Intensity (Counts) | Integrated Int (Counts) |
|---|---|---|---|---|---|---|---|
| 1 | 13 | 17.7561 | 4.99119 | 100 | 0.31900 | 947 | 16049 |
| 2 | 12 | 14.9168 | 5.93423 | 92 | 0.30230 | 867 | 14513 |
| 3 | 15 | 18.8000 | 4.71634 | 80 | 0.65720 | 758 | 31597 |

Peak Data List

| peak no. | 2Theta (deg) | d (A) | I/I1 | FWHM (deg) | Intensity (Counts) | Integrated Int (Counts) |
|---|---|---|---|---|---|---|
| 1 | 4.7340 | 18.65124 | 1 | 0.16140 | 9 | 69 |
| 2 | 5.9215 | 14.91331 | 11 | 0.26490 | 100 | 1723 |
| 3 | 7.0000 | 12.61783 | 3 | 0.20660 | 29 | 563 |

TABLE 8B-continued

| | | | | | |
|---|---|---|---|---|---|
| 4 | 7.5504 | 11.69922 | 29 | 0.44910 | 279 | 6489 |
| 5 | 9.1500 | 9.65724 | 8 | 0.42000 | 76 | 1779 |
| 6 | 10.5600 | 8.37073 | 4 | 0.18660 | 34 | 468 |
| 7 | 11.0208 | 8.02175 | 34 | 0.29110 | 323 | 4468 |
| 8 | 11.1600 | 7.92200 | 30 | 0.56800 | 287 | 7708 |
| 9 | 12.6400 | 6.99756 | 16 | 0.35600 | 147 | 2545 |
| 10 | 12.8400 | 6.88901 | 20 | 0.27840 | 191 | 2234 |
| 11 | 14.5200 | 6.09549 | 9 | 0.16800 | 87 | 1282 |
| 12 | 14.9168 | 5.93423 | 92 | 0.30230 | 867 | 14513 |
| 13 | 17.7561 | 4.99119 | 100 | 0.31900 | 947 | 16049 |
| 14 | 18.3000 | 4.84405 | 73 | 0.40260 | 692 | 12656 |
| 15 | 18.8000 | 4.71634 | 80 | 0.65720 | 758 | 21597 |
| 16 | 19.2077 | 4.61714 | 41 | 0.36220 | 387 | 6608 |
| 17 | 19.5800 | 4.53018 | 63 | 0.34720 | 593 | 11731 |
| 18 | 20.0200 | 4.43159 | 14 | 0.15560 | 130 | 1783 |
| 19 | 20.7824 | 4.27071 | 24 | 0.54170 | 223 | 6510 |
| 20 | 22.0112 | 4.03499 | 26 | 0.47750 | 250 | 6040 |
| 21 | 22.4800 | 3.95190 | 22 | 0.45260 | 211 | 4333 |
| 22 | 23.3273 | 3.81023 | 18 | 0.29470 | 171 | 2718 |
| 23 | 24.1490 | 3.68242 | 24 | 0.51800 | 232 | 6302 |
| 24 | 25.3800 | 3.50653 | 44 | 0.43120 | 413 | 14100 |
| 25 | 25.8930 | 3.43821 | 44 | 0.27980 | 419 | 5539 |
| 26 | 26.2380 | 3.39378 | 24 | 0.79670 | 227 | 8510 |
| 27 | 26.8200 | 3.32144 | 40 | 0.61720 | 383 | 13675 |
| 28 | 27.3087 | 3.26310 | 14 | 0.49680 | 130 | 3097 |
| 29 | 27.7600 | 3.21107 | 18 | 0.42180 | 175 | 4291 |
| 30 | 28.9185 | 3.08501 | 27 | 0.54570 | 258 | 5924 |
| 31 | 29.3200 | 3.04367 | 11 | 0.30660 | 104 | 2021 |
| 32 | 30.3600 | 2.94173 | 13 | 0.65340 | 119 | 4194 |
| 33 | 31.1400 | 2.86980 | 17 | 0.56000 | 159 | 4356 |
| 34 | 32.0000 | 2.79461 | 3 | 0.14140 | 25 | 165 |
| 35 | 32.8233 | 2.72637 | 10 | 0.29330 | 95 | 1976 |
| 36 | 33.8725 | 2.64428 | 7 | 0.55500 | 64 | 1859 |

Figure 5:
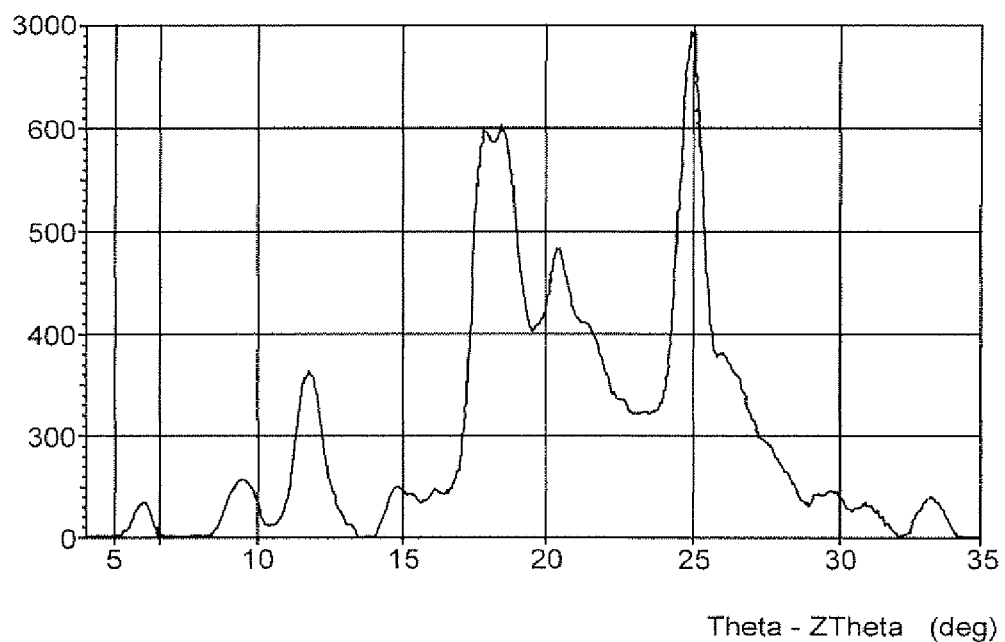
FIG. 5 shows a characteristic XRPD pattern for the succinate salt of Ethyl N—[(S)({[(2R,5R)-5-(6-amino-9H-purin-9-yl)-4-fluoro-2,5-dihydrofuran-2-yl]oxy}methyl) phenoxyphosphinoyl]-L-alaninate.

FIG. 5 shows the characteristic XRPD pattern for the succinate salt. The principal and characteristic peaks that define this crystalline form of the succinate salt are shown in Tables 9A and 9B.

TABLE 9A

Succinate Salt PXRD Peaks

| Strongest Peaks | 2Theta (deg) | d (A) | FWHM (deg) | Integrated Int |
|---|---|---|---|---|
| 1 | 24.91 | 3.5716 | 1.1300 | 40991 |
| 2 | 18.46 | 4.8024 | 3.7340 | 16639 |
| 3 | 17.76 | 4.9901 | 3.4162 | 9106 |

TABLE 9B

* Basic Data Process *

| | |
|---|---|
| Group Name | |
| Data Name | 34984A |
| File Name | 34984A.PKR |
| Sample Name | Lot# 2587-166-27 |
| Comment | Salts USP <941> |

Strongest 3 peaks

| no. | peak no. | 2Theta (deg) | d (A) | I/I1 | FWHM (deg) | Intensity (Counts) | Integrated Int (Counts) |
|---|---|---|---|---|---|---|---|
| 1 | 10 | 24.9100 | 3.57161 | 100 | 1.13000 | 590 | 40991 |
| 2 | 7 | 18.4600 | 4.80243 | 81 | 0.73400 | 480 | 16639 |
| 3 | 6 | 17.7600 | 4.99010 | 79 | 0.41620 | 464 | 9106 |

TABLE 9B-continued

Peak Data List

| peak no. | 2Theta (deg) | d (A) | I/I1 | FWHM (deg) | Intensity (Counts) | Integrated Int (Counts) |
|---|---|---|---|---|---|---|
| 1 | 6.0033 | 14.71029 | 7 | 0.64670 | 43 | 1492 |
| 2 | 9.4308 | 9.37032 | 12 | 1.24830 | 69 | 4432 |
| 3 | 11.7717 | 7.51169 | 33 | 1.08060 | 195 | 11923 |
| 4 | 14.7400 | 6.00500 | 10 | 0.60000 | 60 | 4288 |
| 5 | 16.0720 | 5.51020 | 9 | 0.55880 | 56 | 1470 |
| 6 | 17.7600 | 4.99010 | 79 | 0.41620 | 464 | 9106 |
| 7 | 18.4600 | 4.80243 | 81 | 0.73400 | 480 | 16639 |
| 8 | 20.4772 | 4.33367 | 57 | 0.87020 | 337 | 13869 |
| 9 | 21.4293 | 4.14323 | 43 | 0.40730 | 252 | 4832 |
| 10 | 24.9100 | 3.57161 | 100 | 1.13000 | 590 | 40991 |
| 11 | 26.1400 | 3.40628 | 36 | 2.92000 | 212 | 21458 |
| 12 | 27.9400 | 3.19079 | 16 | 1.47000 | 86 | 8157 |
| 13 | 29.7800 | 2.99769 | 9 | 0.31340 | 53 | 779 |
| 14 | 30.9200 | 2.88972 | 7 | 1.28000 | 40 | 3619 |
| 15 | 33.2223 | 2.69446 | 8 | 1.08670 | 49 | 2527 |

Figure 6:
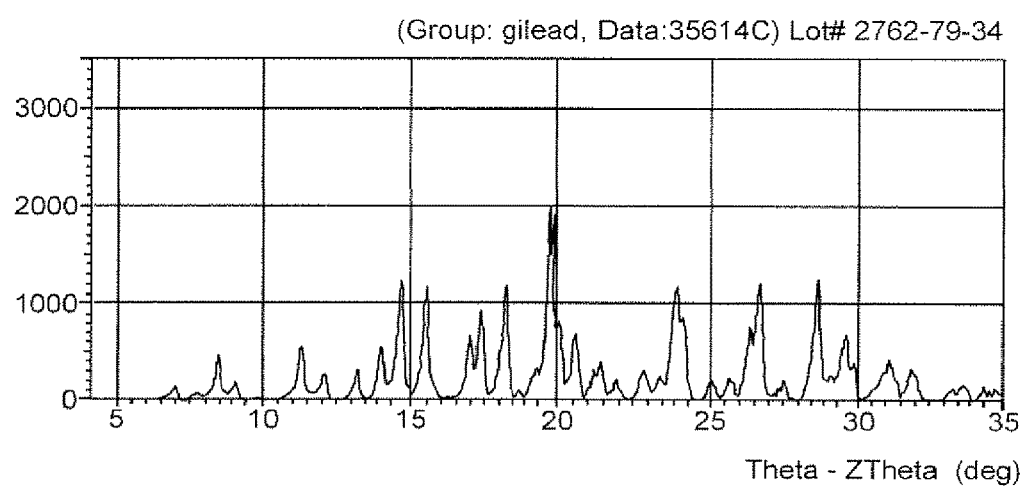
FIG. 6 shows a characteristic XRPD pattern for the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

FIG. 6 shows the characteristic XRPD pattern for the citrate salt. The principal and characteristic peaks that define this crystalline form of the citrate salt are shown in Tables 10A and 10B.

TABLE 10A

Citrate Salt PXRD Peaks

| Strongest Peaks | 2Theta (deg) | d (A) | FWHM (deg) | Integrated Int |
|---|---|---|---|---|
| 1 | 19.81 | 4.4784 | 0.2635 | 14837 |
| 2 | 28.63 | 3.1155 | 0.3312 | 13074 |
| 3 | 14.64 | 6.0465 | 0.2473 | 10572 |

TABLE 10B

* Basic Data Process *

| | |
|---|---|
| Group Name | |
| Data Name | 35614A |
| File Name | 35614A.PKR |
| Sample Nalme | Lot# 2782-76-32 |
| Comment | USP <941> |

Strongest 3 peaks

| no. | peak no. | 2Theta (deg) | d (A) | I/I1 | FWHM (deg) | Intensity (Counts) | Integrated Int (Counts) |
|---|---|---|---|---|---|---|---|
| 1 | 21 | 19.7858 | 4.48352 | 100 | 0.26810 | 1443 | 20538 |
| 2 | 30 | 23.8400 | 3.72944 | 55 | 0.33400 | 793 | 14567 |
| 3 | 35 | 26.5965 | 3.34884 | 51 | 0.31810 | 734 | 11131 |

Peak Data List

| peak no. | 2Theta (deg) | d (A) | I/I1 | FWHM (deg) | Intensity (Counts) | Integrated Int (Counts) |
|---|---|---|---|---|---|---|
| 1 | 6.7400 | 13.10398 | 3 | 0.16360 | 47 | 456 |
| 2 | 6.9496 | 12.70922 | 6 | 0.21930 | 87 | 864 |
| 3 | 8.2200 | 10.74764 | 6 | 0.23120 | 81 | 1414 |
| 4 | 8.4436 | 10.46352 | 18 | 0.22630 | 253 | 2802 |
| 5 | 9.0566 | 9.75662 | 6 | 0.22460 | 89 | 1275 |
| 6 | 11.0600 | 7.99341 | 4 | 0.18000 | 62 | 762 |
| 7 | 11.2871 | 7.83308 | 16 | 0.23720 | 238 | 2770 |
| 8 | 11.8800 | 7.44345 | 4 | 0.19560 | 52 | 603 |
| 9 | 12.0508 | 7.33833 | 8 | 0.25030 | 114 | 1167 |
| 10 | 13.1691 | 6.71758 | 16 | 0.22170 | 229 | 3085 |
| 11 | 13.9959 | 6.32255 | 25 | 0.23910 | 358 | 5182 |
| 12 | 14.6151 | 6.05604 | 33 | 0.26400 | 470 | 7221 |
| 13 | 15.4624 | 5.72604 | 25 | 0.30010 | 356 | 5658 |
| 14 | 15.8200 | 5.59740 | 3 | 0.18800 | 48 | 832 |

TABLE 10B-continued

| | | | | | | |
|---|---|---|---|---|---|---|
| 15 | 16.9600 | 5.22364 | 26 | 0.27100 | 377 | 5496 |
| 16 | 17.3474 | 5.10785 | 46 | 0.26120 | 668 | 9289 |
| 17 | 18.0000 | 4.92411 | 19 | 0.19920 | 271 | 3037 |
| 18 | 19.2200 | 4.86514 | 32 | 0.20420 | 465 | 5224 |
| 19 | 18.7154 | 4.73746 | 4 | 0.21420 | 51 | 606 |
| 20 | 19.2200 | 4.61421 | 10 | 0.19200 | 146 | 2871 |
| 21 | 19.7858 | 4.48352 | 100 | 0.26810 | 1443 | 20538 |
| 22 | 20.0800 | 4.41849 | 38 | 0.19380 | 546 | 6060 |
| 23 | 20.5315 | 4.32233 | 32 | 0.32250 | 455 | 7724 |
| 24 | 21.1200 | 4.20320 | 8 | 0.25500 | 114 | 1667 |
| 25 | 21.4000 | 4.14883 | 16 | 0.26760 | 235 | 3054 |
| 26 | 21.8913 | 4.05682 | 10 | 0.26260 | 141 | 2250 |
| 27 | 22.8001 | 3.89713 | 13 | 0.30110 | 181 | 2641 |
| 28 | 23.2200 | 3.82760 | 3 | 0.19760 | 50 | 746 |
| 29 | 23.3691 | 3.80351 | 6 | 0.16040 | 83 | 625 |
| 30 | 23.8400 | 3.72944 | 55 | 0.33400 | 793 | 14567 |
| 31 | 24.1800 | 3.67776 | 26 | 0.12300 | 380 | 4146 |
| 32 | 25.0296 | 3.55482 | 8 | 0.32290 | 119 | 2002 |
| 33 | 25.6031 | 3.47648 | 7 | 0.22090 | 102 | 1365 |
| 34 | 26.2800 | 3.38845 | 26 | 0.30180 | 379 | 5681 |
| 35 | 26.5965 | 3.34884 | 51 | 0.31810 | 734 | 11131 |
| 36 | 27.4848 | 3.24255 | 6 | 0.20170 | 63 | 1222 |
| 37 | 28.1600 | 3.16636 | 4 | 0.09340 | 58 | 441 |
| 38 | 28.5989 | 3.11875 | 46 | 0.33280 | 666 | 12909 |
| 39 | 29.0484 | 3.07151 | 9 | 0.23960 | 127 | 1440 |
| 40 | 29.5600 | 3.01950 | 20 | 0.48340 | 290 | 6624 |
| 41 | 29.8800 | 2.98789 | 16 | 0.14600 | 235 | 2012 |
| 42 | 30.4400 | 2.93419 | 3 | 0.09340 | 44 | 274 |
| 43 | 30.7800 | 2.90254 | 11 | 0.10020 | 155 | 737 |
| 44 | 31.0600 | 2.87701 | 16 | 0.19060 | 233 | 3504 |
| 45 | 31.3400 | 2.85195 | 4 | 0.18000 | 55 | 802 |
| 46 | 31.5800 | 2.83082 | 4 | 0.12960 | 54 | 357 |
| 47 | 31.8602 | 2.80656 | 12 | 0.36550 | 172 | 2804 |
| 48 | 32.2200 | 2.77603 | 4 | 0.08580 | 55 | 482 |
| 49 | 33.0800 | 2.70580 | 3 | 0.09060 | 50 | 388 |
| 50 | 33.2668 | 2.69103 | 5 | 0.12920 | 65 | 453 |
| 51 | 33.5521 | 2.66571 | 7 | 0.36940 | 108 | 2008 |
| 52 | 34.3755 | 2.60673 | 6 | 0.15550 | 83 | 1053 |

All literature and patent citations above are hereby expressly incorporated by reference at the locations of their citation. Specifically cited sections or pages of the above cited works are incorporated by reference with specificity. While the invention has been described in detail sufficient to allow one of ordinary skill in the art to make and use the subject matter of the following claims, it is also contemplated that certain modifications of the following claims can be made and yet remain within the scope and spirit of the invention.

What is claimed is:

1. A solid oral dosage form comprising darunavir and a therapeutically effective amount of a citrate salt of the compound of formula I:

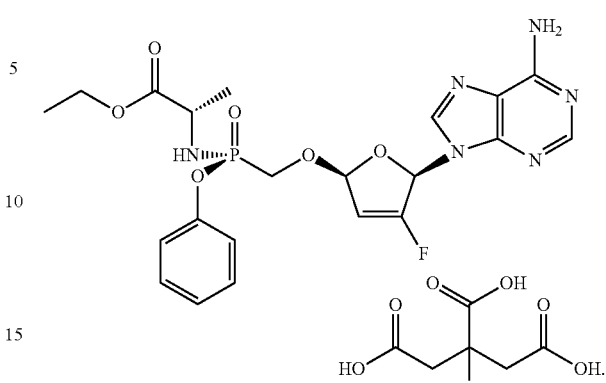

2. The solid oral dosage form of claim 1, further comprising an additional therapeutic agent.

3. The solid oral dosage form of claim 2, wherein the additional therapeutic agent is an HIV integrase inhibitor.

4. The solid oral dosage form of claim 1, wherein the dosage form comprises 10 mg to 30 mg of the citrate salt of the compound of formula I.

5. The solid oral dosage form of claim 1, further comprising at least one excipient selected from lactose, microcrystalline cellulose, croscarmellose sodium, magnesium stearate, povidone, and lactose monohydrate.

6. The solid oral dosage form of claim 1, wherein the dosage form is a tablet.

7. A method of treating HIV infection, comprising administering to a human being in need thereof (a) darunavir and (b) a therapeutically affective amount of a citrate salt of the compound formula I:

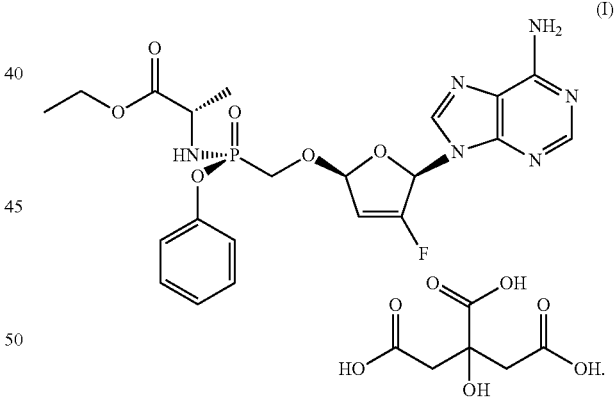

8. The method of claim 7, wherein the darunavir and the citrate salt of the compound of formula I are administered simultaneously, concurrently, separately, or sequentially.

9. The method of claim 7, wherein of the citrate salt of the compound of formula I is administered at a dosage of 10 mg to 30 mg.

10. The method of claim 7, further comprising administering to the human being an HIV integrase inhibitor.

* * * * *